(12) United States Patent
Nagai

(10) Patent No.: US 7,142,637 B2
(45) Date of Patent: Nov. 28, 2006

(54) X-RAY DIAGNOSIS APPARATUS

(75) Inventor: Seiichiro Nagai, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/139,780

(22) Filed: May 31, 2005

(65) Prior Publication Data
US 2005/0207533 A1 Sep. 22, 2005

Related U.S. Application Data

(62) Division of application No. 10/464,764, filed on Jun. 19, 2003.

(30) Foreign Application Priority Data
Jun. 26, 2002 (JP) ............................. 2002-185488

(51) Int. Cl.
*H05G 1/64* (2006.01)

(52) U.S. Cl. .................................. 378/98.8; 250/370.09

(58) Field of Classification Search ................. 378/98, 378/98.8, 116; 348/304; 250/208.1, 370.09
See application file for complete search history.

(56) References Cited

U.S. PATENT DOCUMENTS

| | | | |
|---|---|---|---|
| 4,996,413 A | 2/1991 | McDaniel et al. | |
| 5,818,898 A * | 10/1998 | Tsukamoto et al. | 378/98.8 |
| 6,404,852 B1 * | 6/2002 | Petrick et al. | 378/98.8 |
| 6,657,177 B1 * | 12/2003 | Goto | 250/208.1 |

* cited by examiner

*Primary Examiner*—Courtney Thomas
*Assistant Examiner*—Hoon Song
(74) *Attorney, Agent, or Firm*—Oblon, Spivak, McClelland, Maier & Neustadt, P.C.

(57) ABSTRACT

An X-ray diagnosis apparatus including an X-ray detector which has a plurality of detection elements. On the X-ray detector, there is a first area and a second area. A readout unit reads out an electric charge from a detection element on the first area before reading out the electric charge from a detection element on the second area. A display unit displays an X-ray image data which is created by the electric charge read out from the detection element on the second area.

16 Claims, 20 Drawing Sheets

X-RAY DIAGNOSIS APPARATUS

CROSS-REFERENCE TO RELATED APPLICATIONS

This application is based upon and claims the benefit of priority from prior Japanese Patent Application No. P2002-185488 filed on Jun. 26, 2002, the entire contents of which are incorporated herein by reference.

BACKGROUND OF THE INVENTION

1. Field of the Invention

The present invention relates to an X-ray diagnosis apparatus which has a plurality of detection elements arranged in 2-dimensions.

2. Description of the Related Art

Medical diagnosis imaging technology using X-rays, an magnetic resonance imaging (MRI), X-ray computer tomography (CT), or similar technologies, have rapidly improved with the advancement of computer technologies. An X-ray film and an Image Intensifier (I.I.) are conventionally used in X-ray diagnosis equipment. When using an I.I., X-rays irradiated through a patient are changed to an optical signal by the I.I., and the optical signal is changed to an electrical signal by a TV camera. The electrical signal is then A/D converted and displayed on a TV monitor as an X-ray image. The I.I. makes it possible to image the patient in real time, which cannot be realized by a method using the X-ray film. Further, since the image is obtained as a digital signal in the I.I. method, various types of image processing can be used to further analyze the image.

In some devices, the traditional I.I. has been replaced with an X-ray flat panel detector (hereinafter flat panel detector). A flat panel detector is disclosed in U.S. Pat. No. 5,818,898, the entire contents of which are incorporated herein by reference. Typically, a flat panel detector has 2-dimensional X-ray detection elements. In comparison with the I.I., the flat panel detector is characterized by improved image quality and stability. In a flat panel detector, an electric charge corresponding to an amount of the X-ray irradiation (hereinafter called as a signal charge) accumulates in the 2-dimensional detection elements. The signal charges accumulated in the detection elements are sequentially output via a TFT (Thin Film Transistor) which has a switching function. The output signal is converted to a signal voltage by a charge/voltage converter which is then converted to a digital signal by an A/D converter. The digital signal is stored in an image memory as an X-ray image, and the X-ray image is displayed on the TV monitor. The digital signal of the X-ray image can be used for various processing to the image or subtraction processing between the images.

In conventional flat panel detectors, spurious electric charges caused by stray capacitances between a gate and a source (hereinafter called as a stray charge) accumulate after the TFT changes from ON state to OFF state. Moreover, it is known that an impedance does not become a large value immediately after the impedance between the source and a drain of the TFT changes OFF. Consequently, the stray charge can leak out to the output wire through a gap between the source and the drain, and can thus be inadvertently added to the signal charge output via the TFT. Because the signal charges accumulated in each the detection elements are read according to a similar principle as a TV scan, an amount of the added stray charges (hereinafter called as a total stray charge) increases according to the line number corresponding to the line where the signal charge is read out. That is, the total stray charge is different in each line and is added to the signal charge which is used for making the X-ray image. These accumulating stray charges cause a phenomenon referred to as shading), whereby each line is corrupted with different brightnesses, making the image quality low.

SUMMARY OF THE INVENTION

The present invention intends to solve the above-mentioned problems by restraining the shading effect caused by stray charges so as to provide flat panel X-ray devices with improved image quality. Accordingly, one aspect of the present invention provides an X-ray diagnosis apparatus comprising an X-ray source configured to irradiate an X-ray to an object, an X-ray detector including a plurality of detection elements which are arranged in a first direction and a second direction and which are configured to detect an X-ray penetrating through the object and to change the X-ray to an electric charge, a readout unit configured to read out the electric charge from the detection element on a second area before reading out the electric charge from the detection element on a first area, a signal converter configure to convert the electric charge read out from the detection element on the first area to an X-ray image, and display unit configured to display the X-ray image.

Another aspect of the present invention provides an X-ray diagnosis apparatus comprising an X-ray source configured to irradiate an X-ray to an object, an X-ray detector including a plurality of detection elements which are arranged in a first direction and a second direction and which are configured to detect an X-ray penetrating through the object and to change the X-ray to an electric charge, a readout unit configured to read out the electric charge from the detection element on a second area before reading out the electric charge from the detection element on a first area, a signal converter configure to convert the electric charge read out from the detection element on the first area to an X-ray image data, and a display unit configured to display the X-ray image data, wherein the first area is separated to a plurality of areas in the second direction, and the readout unit reads out the electric charges from the plurality of areas in the second direction in a predetermined sequence.

Another aspect of the present invention provides an X-ray diagnosis apparatus comprising an X-ray source configured to irradiate an X-ray to an object, an X-ray detector including a plurality of detection elements which are arranged in a first direction and a second direction and which are configured to detect an X-ray penetrating through the object and to change the X-ray to an electric charge, a controller configured to set a maximum imaging area of the object to be within a first area of the X-ray detector, an input unit configured to input an imaging area of the object within the set maximum imaging area, a readout unit configured to read out the electric charge from the detection element on a second area which is outside of the first area before reading out the electric charge from the detection element on the imaging area, a signal converter configure to convert the electric charge read out from the detection element on the imaging area to an X-ray image data, and a display unit configured to display the X-ray image data.

Another aspect of the present invention provides an X-ray diagnosis apparatus comprising an X-ray source configured to irradiate an X-ray to an object, an X-ray detector including a plurality of detection elements which are arranged in a first direction and a second direction and which are configured to detect an X-ray penetrating through the object to change the X-ray to an electric charge, a readout unit configured to read out the electric charge from the detection element on a second area before reading the electric charge from the detection element on a first area, an amplifier configured to cut the electric charge read out from the detection element on the second area and to amplify the electric charge read out from the detection element on at least a part of the first area, a signal converter configure to convert the amplified electric charge to an X-ray image data, and a display unit configured to display the X-ray image data.

Another aspect of the present invention provides an X-ray diagnosis apparatus comprising an X-ray source configured to irradiate an X-ray to an object, an X-ray detector including a plurality of detection elements which are arranged in a first direction and a second direction and which are configured to detect the X-ray penetrating through the object to change an X-ray to an electric charge, an input unit configured to input an imaging area of the object, a readout unit configured to read out the electric charge from the detection element on a second area before reading the electric charge from the detection element on a first area, an amplifier configured to amplify the electric charge read out from the detection element on the imaging area in an amplification range determined based on a parameter of the imaging area (e.g., imaging area size, shape, total number of detectors, length, width, radius, circumference, number of detectors in a lengthwise direction, number of detectors in a lateral direction, number of detectors in a radial direction, number of a first type of detector, ratio of a first type of detector to a second type of detector, etc.), a signal converter configure to convert the amplified electric charge to an X-ray image data, and a display unit configured to display the X-ray image data.

Another aspect of the present invention provides a method for controlling an X-ray diagnosis apparatus comprising irradiating an X-ray to an object, detecting an X-ray penetrating through the object to change the X-ray to an electric charge by an X-ray detector including a plurality of detection elements which are arranged in a first direction and a second direction, reading out the electric charge from the detection element on a second area before reading the electric charge from the detection element on a first area by a readout unit, converting the electric charge read out from the detection element on the first area to an X-ray image by a signal converter, and displaying the X-ray image by a display unit.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. Wherever possible, the same reference numbers will be used throughout the drawings to the same or the like parts. In the drawings.

DETAILED DESCRIPTION OF THE INVENTION

Figure 1:
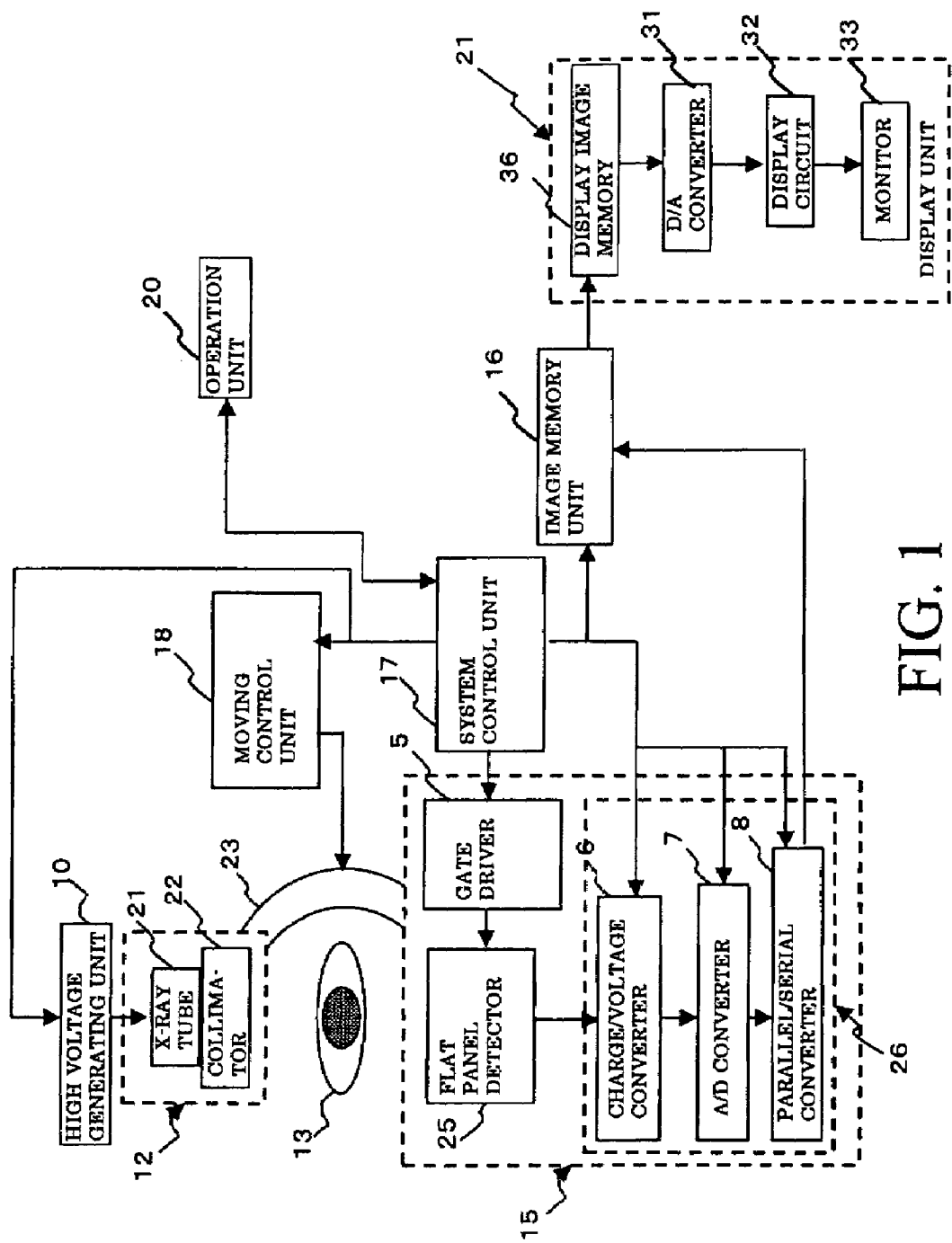
FIG. 1 is a block diagram of an X-ray diagnosis apparatus in a first, second and third embodiments.

A first embodiment of the present invention will be explained, referring to FIG. 1 through FIG. 10. FIG. 1 is a block diagram of an X-ray diagnosis apparatus. The X-ray diagnosis apparatus includes an X-ray generating unit 12, an X-ray detection unit 15, a supporting unit 23 for supporting both units, a moving control unit 18 for controlling movement of the supporting unit 23, and an image memory unit 16 for storing X-ray image data read out by each line. Further, the X-ray diagnosis apparatus includes a display unit 21 which displays the X-ray image data stored in the memory unit 16, a high voltage generating unit 10 for generating a high voltage to irradiate the X-ray from the X-ray generating unit 12, a system control unit 17 which controls each the above mentioned units, and an operation unit 20 by which an operator gives an instruction. The high voltage generating unit 10 generates a high voltage between an anode and a cathode to accelerate a heat electron generated from the cathode of an X-ray tube 21. The X-ray generating unit 12 includes the X-ray tube 21 which irradiates the X-ray to a patient 13 and a collimator 22 which collimates the irradiated X-ray. The X-ray tube 12 has a vacuum tube in which the heat electron accelerated by the high voltage hits a tungsten target to generate the X-ray. The collimator 22 is positioned between the X-ray tube 21 and the patient 13 and collimates the irradiated X-ray to an arbitrary size to make the X-ray image clear.

The X-ray detection unit 15 includes a flat panel detector 25 which changes the X-ray penetrating through the patient 13 to an electric charge and accumulates the electric charge, a gate driver 5 which reads out the accumulated electric charge in the flat panel detector 25 as an X-ray image signal, and an image data generation unit 26 which changes the read out electric charge into image data. On the flat panel detector 25, there is a valid area 40 where detection elements are arranged and an invalid area 41 where detection elements that is the same architecture as the detection elements on the valid area are arranged. The valid area 40 and the invalid area 41 are arranged in a column direction, and the gate driver 5 reads out the electric charge from the invalid area 41 prior to the valid area 40. Details of the X-ray detection unit 15 will be explained later. The moving control unit 18 controls movement of the supporting unit 23 by a control signal from the system control unit 17 to move the X-ray generating unit 12 and the X-ray detection unit 15 at an appropriate position for imaging. The image memory unit 16 sequentially stores the X-ray image data sent from a parallel/serial converter 8 in the X-ray detection unit 15 to make the X-ray image. The display unit 21 includes a display image memory 36, a D/A converter 31, a display circuit 32, and a monitor 33. The X-ray image data stored in the image memory unit 16 is temporally transferred to the display image memory 36, is converted to an analog signal by the D/A converter 31, and is changed to a TV format signal by the display circuit 32 to be displayed on the monitor 33. The system control unit 17 controls a whole system, such as collection of the X-ray image data, control of the display unit 21, and control of the movement of the supporting unit 23. The operation unit 20 includes various kinds of switches and buttons, a keyboard, and a display panel, etc., and the operator instructs conditions of the imaging, such as an imaging area, start of the imaging, and movement of the supporting unit with the operation unit 20. Control signals of the instructions are sent to each unit via the system control unit 5.

Figure 2:
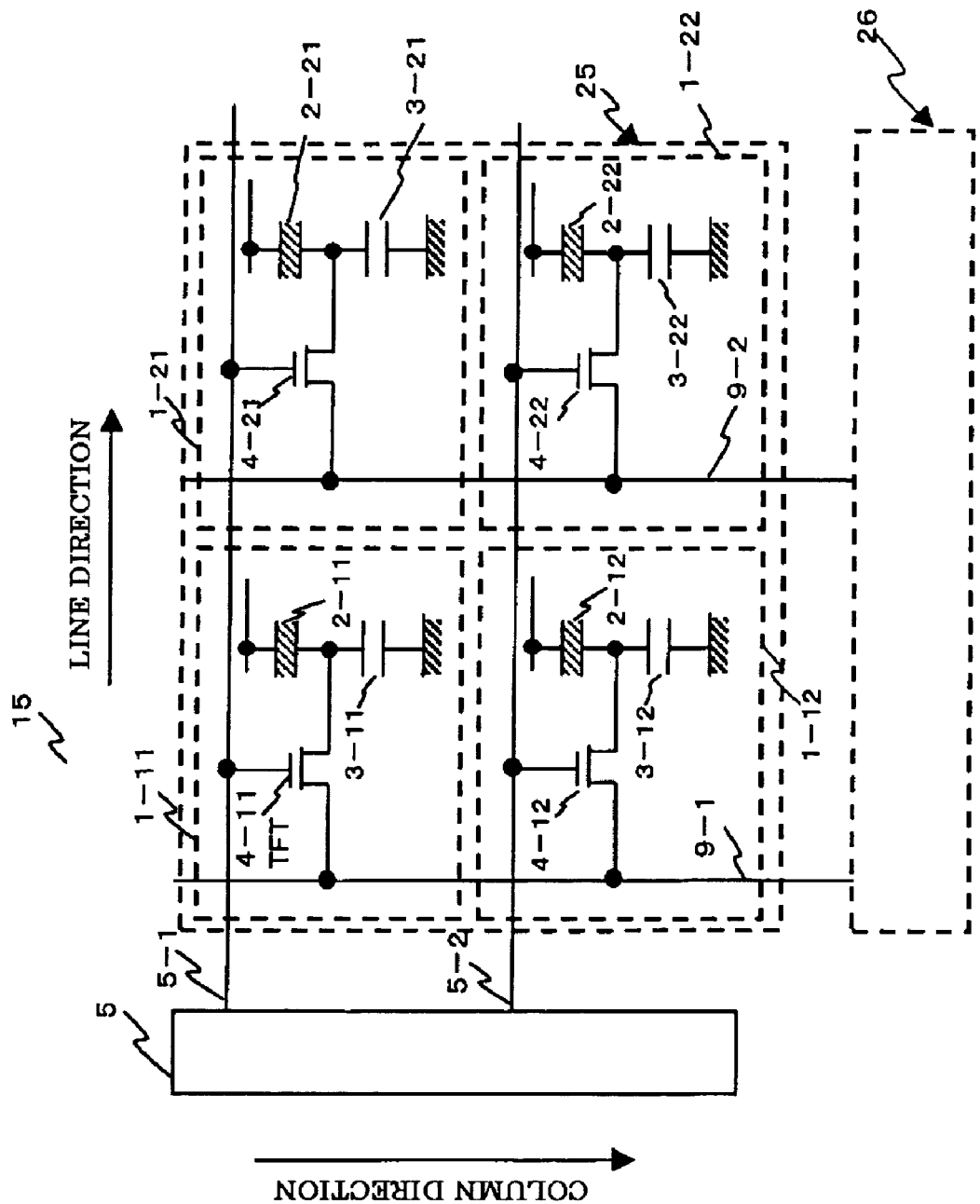
FIG. 2 is a block diagram of a flat panel detector.

An operation and a configuration of the X-ray detection unit 15 are explained referring to FIGS. 1 and 2. The X-ray detection unit 15 includes the flat panel detector 25 which changes the X-ray penetrating the patient 13 into the electric charge, the gate driver 5 which reads out the electric charge accumulated in the flat panel detector 25 as an X-ray image signal, and the image data generation unit 26 which changes the read out electric charge into the image data. The image data generation unit 26 includes a charge/voltage converter 6 which converts the electric charge read out from the flat panel detector 25 into the voltage, the A/D converter 7 which converts the voltage outputting from the charge/voltage converter 6 into the digital signal, and the parallel/serial converter 8 which converts a parallel signal read out from the flat panel detector 25 by a line in parallel into a serial signal. As shown in FIG. 2, the flat panel detector 25 has a plurality of the small detection elements 1 which are 2-dementionally arranged in a line direction and a column direction. The detection element 1 includes photoelectric film 2 which detects the X-ray to generate the electric charge corresponding to the amount of the X-ray, a storage capacitor 3 which accumulates the electric charge generated in the photoelectric film 2, and a TFT 4 (Thin Film Transistor) which reads out the electric charge accumulated in the storage capacitor 3 at the predetermined intervals. The gate driver 5 supplies a pulse signal to a gate terminal of the TFT 4 in order to read out the electric charge accumulated in the storage capacitor 3. The charge/voltage converter 6 converts the electric charge read out from the detection element 1 into the voltage, and the A/D converter 7 converts the voltage into a digital signal. A memory in the parallel/serial converter 8 temporally stores the digital signal which is inputted in parallel by a line, and sequentially outputs the signal.

As shown in FIG. 2, the flat panel detector 25 includes the small detection elements 1 which are 2-dimensionally arranged in the column direction (up and down direction in FIG. 2) and the line direction (right and left direction in FIG. 2). That is, an arrangement direction of detection elements which are connected to the common gate terminal of the gate driver 5 is the line direction, and an arrangement direction of detection elements which are connected to the common output wire 9 is the column direction. In order to make an explanation easy, FIG. 2 shows two column detection elements and two lines detection elements. The detection elements 1-11, 1-12, 1-21, and 1-22 respectively includes the photoelectric films 2-11, 2-12, 2-21, and 2-22, each of which generates the electric charge according to the amount of the X-ray, the storage capacitors 3-11, 3-12, 3-21, and 3-22, each of which accumulates the electric charge, and the TFTs 4-11, 4-12, 4-21, and 4-22, each of which reads out the accumulated electric charge at predetermined intervals. First terminals of the photoelectric films 2-11, 2-12, 2-21, and 2-22 respectively are connected to first terminals of the storage capacitors 3-11, 3-12, 3-21, and 3-22. These connections between the detection elements and the photoelectric films are respectively connected to source terminals of the TFTs 4-11, 4-12, 4-21, and 4-22. Second terminals of the photoelectric films 2-11, 2-12, 2-21, and 2-22 are connected to a bias electrical supply, and second terminals of the storage capacitors 3-11, 3-12, 3-21, and 3-22 are grounded. The gate terminals of the TFTs 4-11 and 4-21 arranged in the line direction are connected to the gate terminal 5-1 of the gate driver 5, and the gate terminals of the TFTs 4-12 and 4-22 arranged in the line direction are connected to the gate terminal 5-2 of the gate driver 5.

Furthermore, drain terminals of the TFTs 4-11 and 4-12 arranged in the column direction are connected to the common output wire 9-1, and drain terminals of the TFTs 4-21 and 4-22 are connected to the common output wire 9-2. The electric charges from the output wires 9-1 and 9-2 are sent to the charge/voltage converter 6 in the image data generation unit 26 to be changed to the voltage corresponding to an amount of the electric charge. When the X-ray penetrating through the patient 13 is incident upon the flat panel detector 25, the signal charges of the size corresponding to the amount of the X-ray are generated in the photoelectric films 2-11, 2-12, 2-21 and 2-22. The signal charges are accumulated in the storage capacitors 3-11, 3-12, 3-21 and 3-22. The gate driver 5 selectively supplies the pulse signal to the gate terminals 5-1 and 5-2 to selectively read out the electric charge by a line. When ON voltage (H level) of the pulse is impressed to the gate of the TFT 4, a state between the drain and source of the TFT 4 switches into a conducting state. The signal charge accumulated in storage capacitors 3-11, 3-12, 3-21 and 3-22 are read out to the output wire 9-1 and 9-2. For example, when the gate terminal 5-1 of the gate driver 5 is impressed ON voltage, the signal charge accumulated in the storage capacitor 3-11 is output to the output wire 9-1. Similarly, when the gate terminal 5-1 of the gate driver 5 is impressed ON voltage, the signal charge accumulated in the storage capacitor 3-21 is output to the output wire 9-2. The signal charges on the output wires are temporally stored in the memory of the parallel/serial converter 8 via the charge/voltage converter 6 and the A/D converter 7. The system control unit 17 serially reads out the data of the detection elements 1-11 and 1-21 from the memory of the parallel/serial converter 8, and the data is stored in the image memory unit 16 as a first line image data.

Next, when the gate terminal 5-1 of the gate driver 5 turns OFF and the gate terminal 5-2 turns ON, the signal charge accumulated in the storage capacitors 3-12 and 3-22 on a second line is read out to the output wire 9-1 and 9-2 via the TFTs. The signal charges on the second line are similarly stored in the memory of the parallel/serial converter 8 via the charge/voltage converter 6 and the A/D converter 7. The system control unit 17 serially reads out the data of the detection elements 1-12 and 1-22 from the memory of the parallel/serial converter 8, and the data is stored in the image memory unit 16 as the second line image data. Thus, the gate driver 5 sequentially impresses the ON voltage to the terminals, namely the lines, and the signal charges of detection elements 1 on the selected line are read out to the output wire 9 in parallel. Based on the control of the system control unit 17, the signal charge is converted to the voltage which is converted to the digital signal. The digital signal is converted to the serial signal to be stored in the image memory unit 16. Similarly, another line is selected, and the electric charges on the selected line are read out in parallel. The read out operation is repeatedly performed to obtain the data of one image.

Figure 3A:
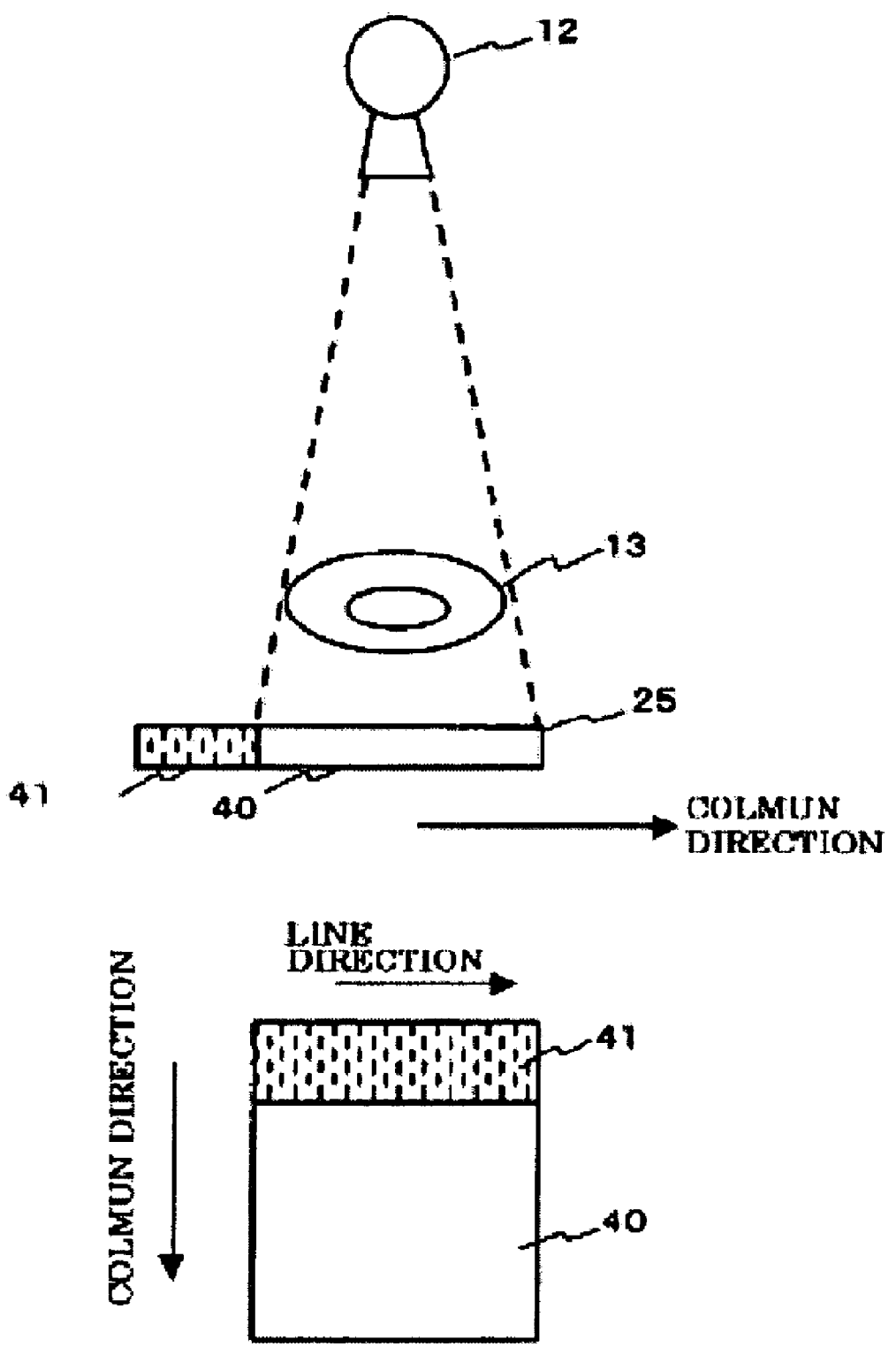
FIG. 3A shows an area of an X-ray irradiation in the first embodiment.
Figure 3B:
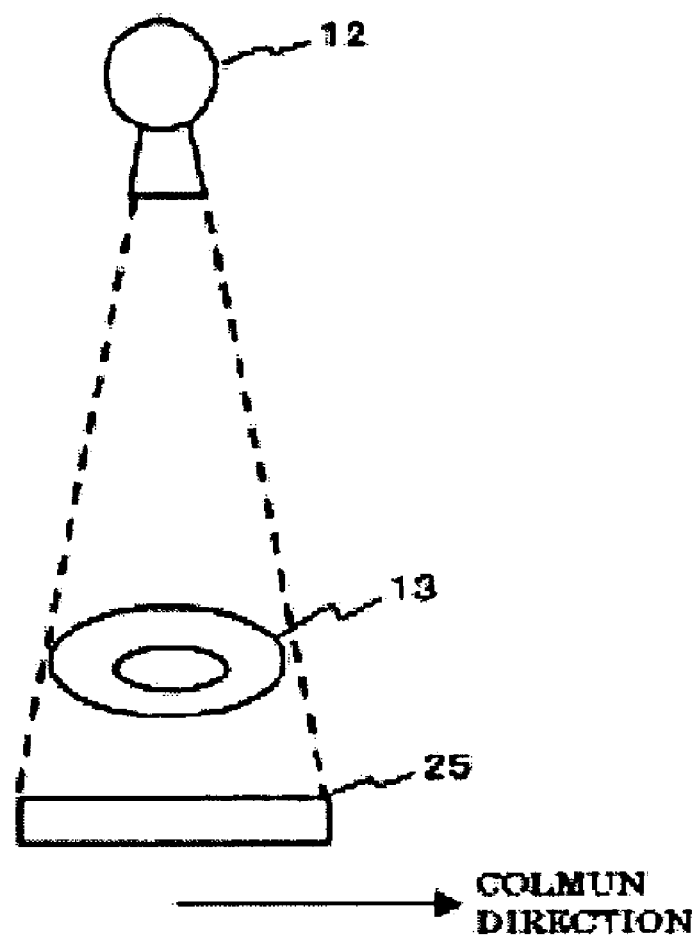
FIG. 3B shows a area of an X-ray irradiation in a prior art.
Figure 3B:
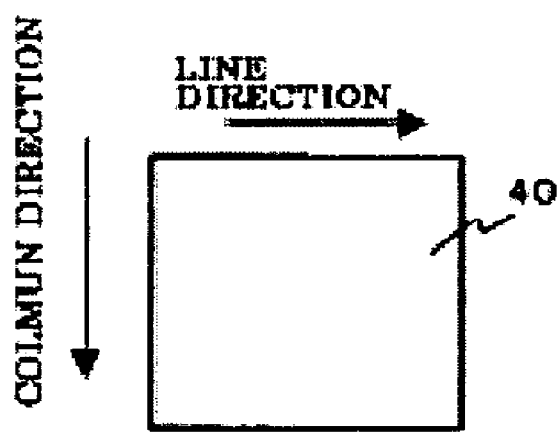

An operation of the X-ray diagnosis apparatus in the first embodiment will be explained referring to FIG. 1. Before imaging, the operator operating the X-ray apparatus sets the conditions of the imaging with the operation unit 20, and controls the moving control unit 18 via the system control unit 17 such that the X-ray generating unit 12 and the X-ray detection unit 15 are positioned at an imaging part of the patient 13. The operator inputs the start command of an X-ray angiography imaging. When the start command is sent to the system control unit 17 from the operation unit 20, the system control unit 17 sends the pulse signal to the high voltage generating unit 10. Based on an output of the high voltage generating unit 10, the X-ray tube 12 irradiates the pulse X-ray toward the patient 13. The X-ray penetrating through the patient 13 is detected by the flat panel detector 25 in the X-ray detection unit 15 which is positioned in back of the patient 13. FIG. 3A shows a method for positioning the flat panel detector 25 in the first embodiment, while FIG. 3B shows a method in a prior art. In both FIGS. 3A and 3B, an area of the X-ray irradiation is set as maximum. By using the conventional positioning method shown in FIG. 3B, when the X-rays irradiated from the X-ray generating unit 12 penetrates through the patient 13 to make the image on the flat panel detector 25, almost all area of the flat panel detector 25 are used for collecting the signal charge generated by the X-ray irradiation to make the image. On the other hand, in the method shown in FIG. 3A in the first embodiment, the flat panel detector 25 has the valid area 40 where the signal charges are used for imaging and the invalid area 41 where the signal charges are not used for imaging. A configuration of the detection elements on the invalid area is the same as the detection elements on the valid area. The invalid area is adjacent to the valid area in the column direction and is driven prior to the valid area. It the first embodiment, an adjustable maximum area corresponds to the valid area on the flat panel detector 25. That is, the operator can set the imaging area without considering the invalid area 41. At this time, the signal charge from the invalid area is not used for the image. The signal charge read from the valid area 40 and the outputted stray charge during reading out the signal charge from the valid area 40 are used for the image. That is to say, an area where the signal charge is not used for imaging, but the stray charge is used, is called as the invalid area 41. On the other hand, both of the signal charge and the stray charge are used for imaging is called as the valid area 40. The charges from the invalid area 41 are used to adjust a size of the total stray electric charge between the lines, where the adjusted charge is subsequently added to the signal charge in the valid area 40.

Figure 4:
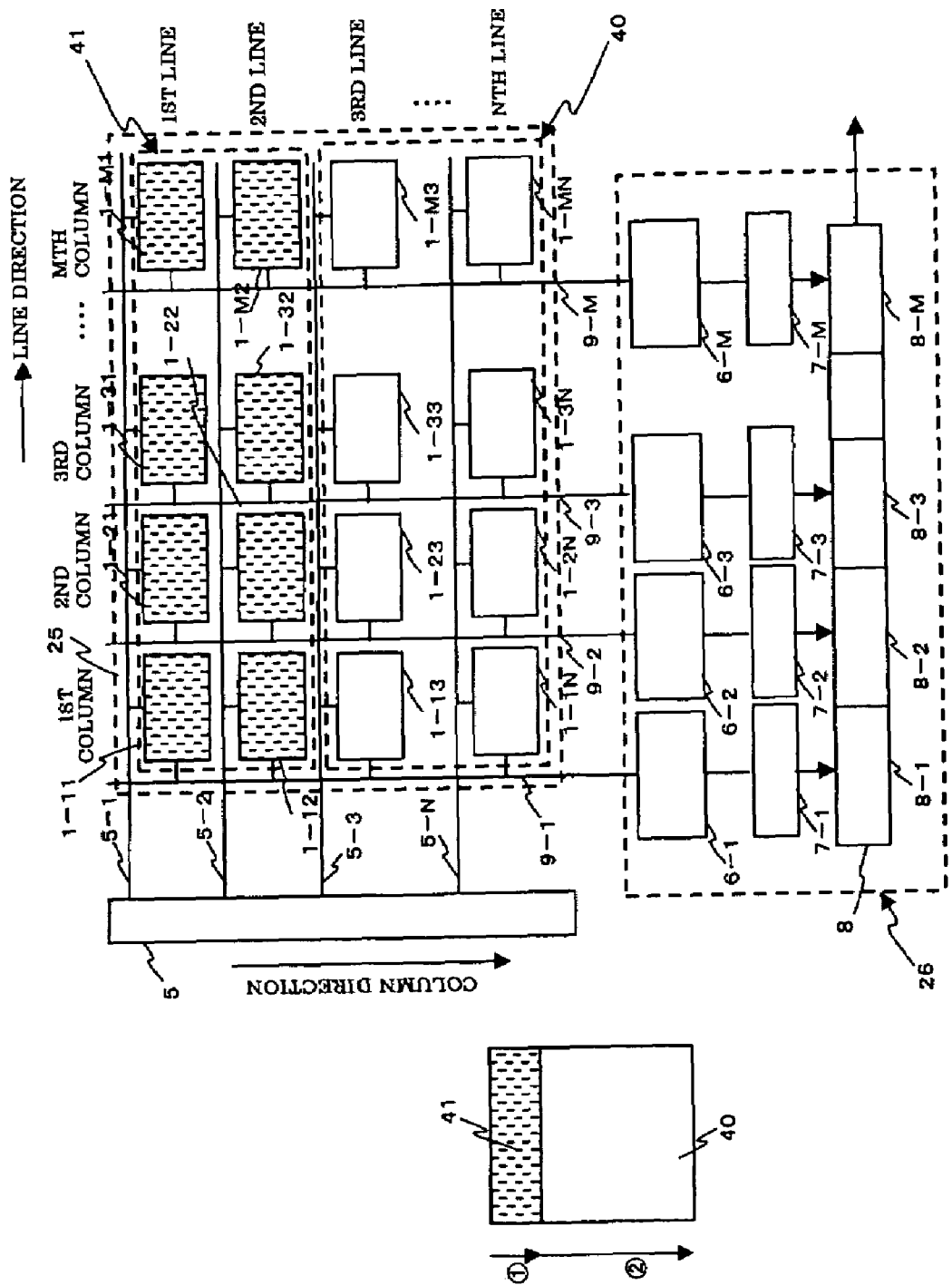
FIG. 4 is a block diagram of a flat panel detector in the first embodiment.

Next, referring to FIG. 4 to FIG. 6, a generating process of the X-ray image obtained by the flat panel detector 25 in the method shown in FIG. 3A will be explained below. In FIG. 4, the flat panel detector 25 which includes the valid area 40 and the invalid area 41 has the detection elements 1 arranged 2 dimensions in M pieces in the line direction and the N pieces in the column direction. In order to make an explanation easily, the two invalid lines are shown as a first line, 1-11, 1-21, and 131 . . . 1M1, and a second line, 1-12, 1-22, 132 . . . 1M2, however the invalid lines are desirably some dozens of lines. Therefore, the valid area 40 is from a third line to Nth line in the FIG. 4. In the flat panel detector 25, M driving terminals (the gate terminal in FIG. 2) of the detection elements on the same line are commonly connected to the same output terminal of the gate driver 5. For example, the output terminal 5-1 of the gate driver 5 is connected to respective driving terminals of the detection elements, 1-11, 1-21, 131 . . . 1M1, and the output terminal 5N is connected to respective driving terminals of the detection elements, 11N, 12N, 13N . . . 1MN. N output terminals (the drain terminal in FIG. 2) of the detection elements on the same column are commonly connected to the same output wire 9 which is connected to an input terminal of the charge/voltage converter 6 in the image data generation unit 26. For example, the output terminals 1-11, 1-12, 113 . . . 11N of the detection elements are commonly connected to the same output wire 9-1 which is connected to the charge/voltage converter 61. Similarly, the output terminals of the detection elements 1M1, 1M2, 1M3 . . . 1MN are commonly connected to the same output wire 9M which is connected to the charge/voltage converter 6M.

Figure 5:
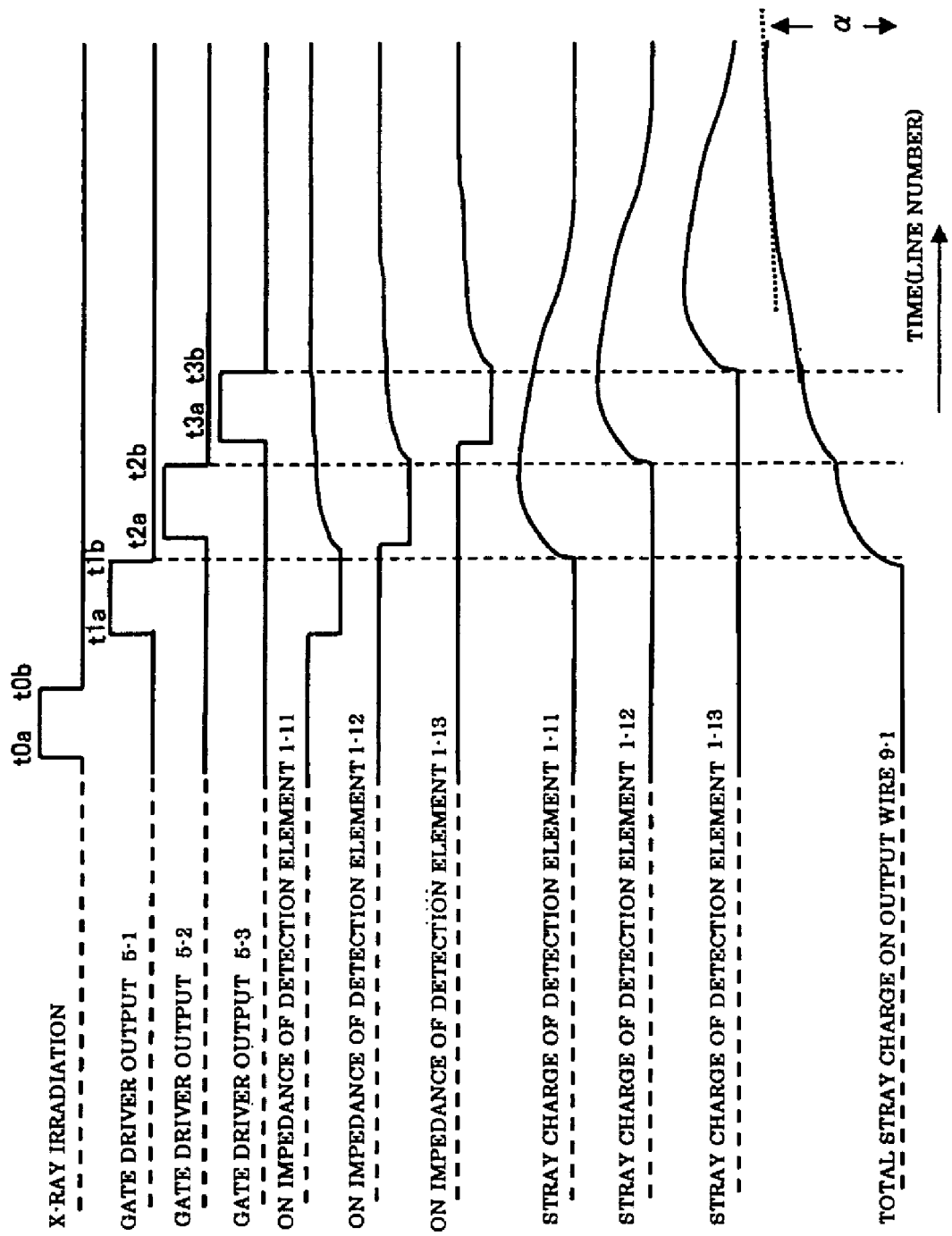
FIG. 5 is a timing chart for explaining an order of generation of a stray charge in the first embodiment.
Figure 6:
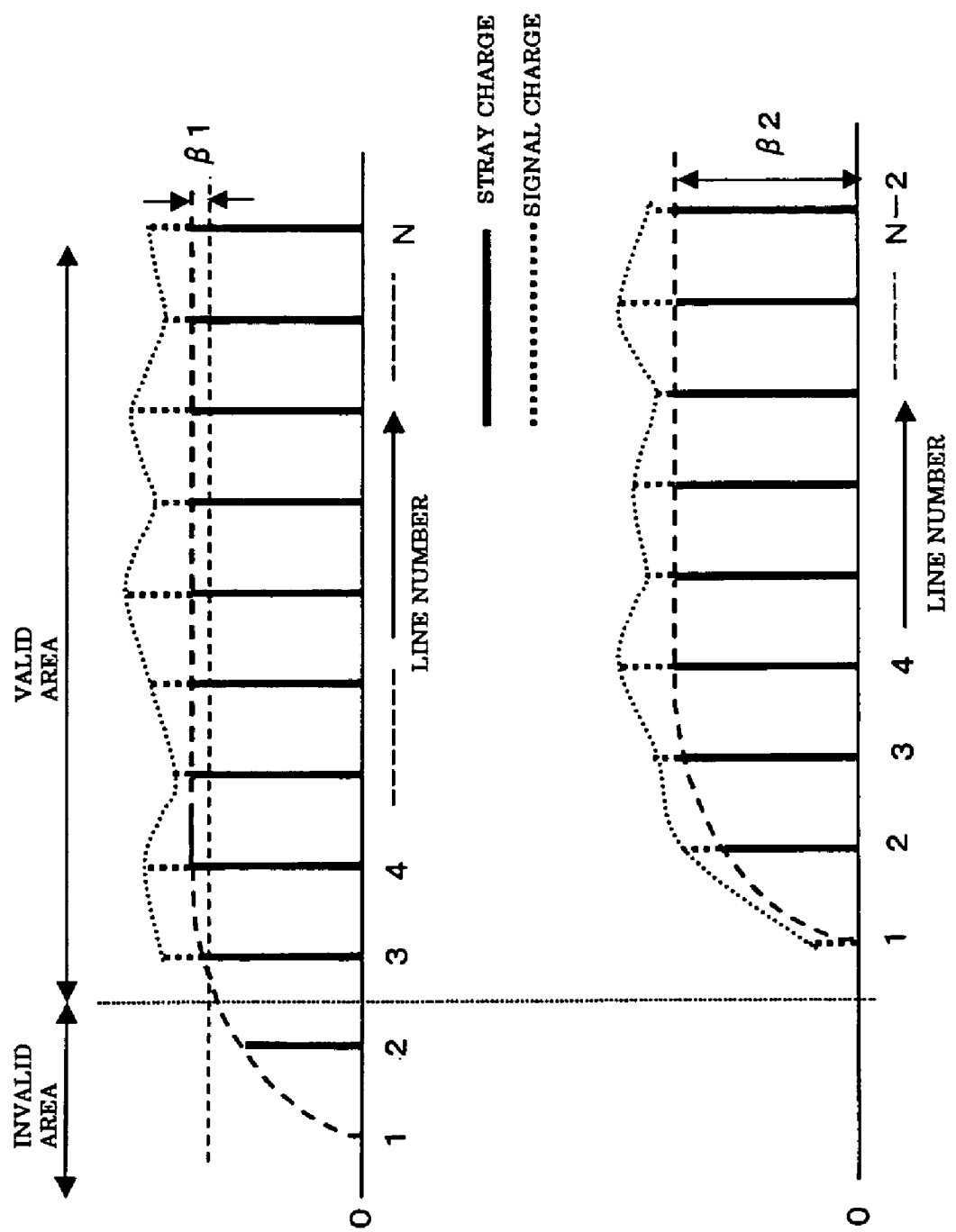
FIG. 6 is a graph for explaining a signal charge and the stray charge.

FIG. 5 shows a time change of an ON resistance of the detection element 1 of the first line to the output of the gate driver 5, the stray charge and the signal charge. A first row from above in FIG. 5 shows a timing of the X-ray irradiation, a second to a forth rows show timings of the outputs from the gate terminals 5-1 to 53. A fifth row to seventh row show the ON resistance between the drain terminal and the source terminal of the detection elements 1-11, 1-12 and 113. An eighth row to tenth row show respective sizes of the stray charges outputted the output wire 9-1 via connections between the source and the drain of the detection elements 1-11, 1-12, 113. An eleventh row shows a size of the total stray outputted from the detection elements 1-11, 1-12, 113 to the output wire 9-1. A horizontal axis in FIG. 5 shows a time axis corresponding to a read out line number.

Based on the control signal from the system control circuit 17, the X-ray generating unit 12 irradiates the X-ray to the patient 13 during the t0*a* to t0*b*. The detection elements 1 arranged on the valid area 40 receive the X-ray which penetrates the patient 13, and accumulates the signal electric charge corresponding to the amount of the X-ray in the storage capacitor 3. After the X-ray irradiation is completed, the system control unit 17 supplies a clock pulse to the gate driver 5, and the gate driver 5 outputs the driving pulse, as shown in the 2nd to 4th rows of FIG. 5, from the gate terminal 5-1 to 5N. As described above, the gate diver 5 supplies the driving pulse (ON voltage) to the gate terminal of the TFT 4 in order to read out the electric charge accumulated in the detection element 1 to the signal output wire 9. Based on the driving pulse to the gate terminal the TFT 4 turns ON state and the charge signal accumulated in the storage capacitor 3 is read out to the output wire 9-1.

Since the resistance between the source and the drain is very low when the gate of TFT4 in the detection element 1 has the ON voltage applied, a voltage of the storage capacitor 3 is almost the same as a voltage of the output wire 9-1. Therefore, the influence of the stray capacitance is small, and almost only the signal charge is read out to the output wire 9. On the other hand, when the OFF voltage is applied to the gate of TFT4 and the TFT4 changes from the ON state to the OFF state, the stray charge caused by the stray capacity starts to accumulate. However the impedance between the source and the drain of the TFT4 increases gradually, as shown in the fifth to the seventh rows of FIG. 5. For this reason, for a while after the TFT4 changes to the OFF state, the stray electric charge passes through between the source and the drain, and is outputted to the signal output wire 9. As shown in FIG. 5, after the X-ray irradiation, the terminals 5-1 of the gate driver 5 turn the ON state (shown as the third row in FIG. 5) during t1a to t1b, and the detection element 1-11 on the first line of the invalid area 41 is driven. Next, the terminal 5-2 of the gate driver 5 turns the ON state during t2a to t2b as shown in the third row of FIG. 5, and the detection element 1-12 is driven. At this time, the terminal 5-1 is in the OFF voltage, and the stray charge caused by the stray capacitance starts to accumulate in the storage capacitor 3-11. The stray charge passes through between the source and the drain of the TFT 4-11 which the impedance is still low (shown as the fifth row of the FIG. 5), and is outputted to the output wire 9-1 (shown as the fifth row of the FIG. 5). Actually, a period when the stray electric charge is outputted to the signal output wire 9 is some dozens times a term (t1a to t1b shown in FIG. 5), however in order to make an explanation easily, the period is shown as approximately 1/10 times in FIG. 5.

Furthermore, the terminal 53 of the gate driver 5 turns in the ON voltage during t3a to t3b (shown as the forth row of the FIG. 5), and the signal charge accumulated in the detection element 13 on the third line of the valid are 40 is outputted to the output wire 9-1. At this time, the stray charge generated in the detection element 1-11 is added to the signal charge generated in the detection element 1-12 and is outputted to the common output wire 9-1 together. That is, on the output wire 9-1, the stray charge of the detection element 1-11 caused by the driving pulse during t1a to t1b and the stray charge of the detection element 1-12 caused by the driving pulse during t2a to t2b are added to the signal charge of the detection element driven by the driving pulse during t3a to t3b. The total values of the signal charge and the stray charge is temporally stored in the memory 81 to 8M of the parallel/serial converter 8 via the charge/voltage converters 61 to 6M and the A/D converters 71 to 7M. Similarly, regarding the second column to Mth column, the stray charges generated in the first and the second lines on the invalid are 41 are added to the signal charge generated in the third line on the valid area 40, and the total values of the stray charge and the signal charges are outputted to the output wires 9-2 to 9M. The total charge is A/D converted and is stored in the memory 9-2 to 9M of the parallel/serial converter 8. Thus, the signal charges obtained during t3a to t3b are temporally stored in the memory 81 to 8M of the parallel/serial converter 8 as the third line data (namely, a first line data in valid area 40), and are stored in the image memory unit 16. Similarly, the output terminals 54 to 5N turns in the ON voltage in order, the signal charges accumulated in the detection elements on the forth line to Nth line are outputted to the output wires 9-1 to 9M. For a while after the driver terminals 54 to 5N turns in the OFF voltage, the stray charges are outputted to the output wire 9-1 to 9M. Therefore, as shown in the eleventh row of FIG. 5, according to the line number, the stray charge generated in the detection element 1 on the first line of the flat panel detector 25 is outputted to the output wire 9-1. The total value of the stray charge is temporally stored in the parallel/serial converter 8 via the charge/voltage converters 61 to 6M and the A/D converters 71, and is stored in the image memory unit 16 as the forth to Nth lines image data. After the X-ray image data is created in the image memory unit 16, based on the control of the system control unit 17, the display image memory 36 of the X-ray tube 21 stores the X-ray image data. The X-ray image data is D/A converted by the D/A converter 31 and is changed to the TV format signal by the display circuit 32. The TV format signal is displayed on the monitor 33 as the X-ray image.

Figure 7:
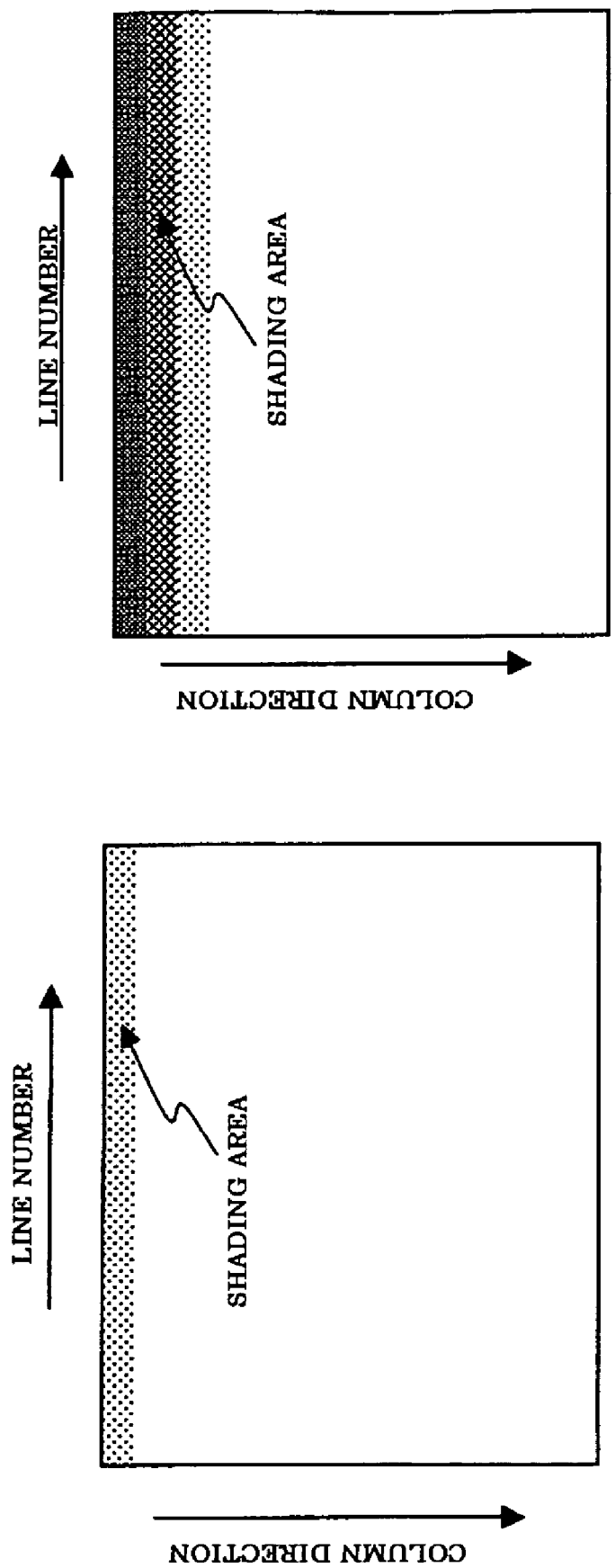
FIG. 7 shows a shading area on an X-ray image in the first embodiment.

In the meanwhile, rate of change of the total stray charge on the output wire 9-1 per unit of time is a maximum value immediately after the signal charge generated in the detection element on the first line is read out, and the changing rate approaches to a constant value α according to the line number. For ease of explanation, in the eighth to eleventh rows of FIG. 5, only the stray charge and the total stray charge are shown. In FIG. 6, the total stray charge corresponding to the line number is shown as a continuous line and the signal charge added to the total stray charge is shown as a broken line. On the upper side of FIG. 6, the total stray charge and signal charge of the output wire 9-1 in the first embodiment is shown. On the lower side of FIG. 6, the total stray charge and signal charge in a conventional method is shown. As described above, the X-ray image data is created from the signal charge on the third to Nth lines in the first embodiment, however the X-ray image data is created from the signal charge on the first to Nth lines in the conventional method. Therefore, the rate of change of the total stray charge ($\beta 1$) of the X-ray imaging data in the first embodiment, as shown on the upper side of FIG. 6, is lower than the rate of change ($\beta 2$) in the conventional method, as shown on the lower side of FIG. 6, and, thus, the first embodiment provides for reduced shading as compared to the conventional art. FIG. 7 compares the shading effect of both the first embodiment and the conventional method. In this Figure, the shading appears on lines of small number, however the shading is reduced in the first embodiment in comparison with the conventional method. That is to say, since the electric charge on the invalid area is read out prior to the valid area in the first embodiment, the stray charge is saturated when the signal charge in each line on the valid area is read out. Therefore, the difference of light and darkness is lower, and the shading is reduced.

Figure 8A:
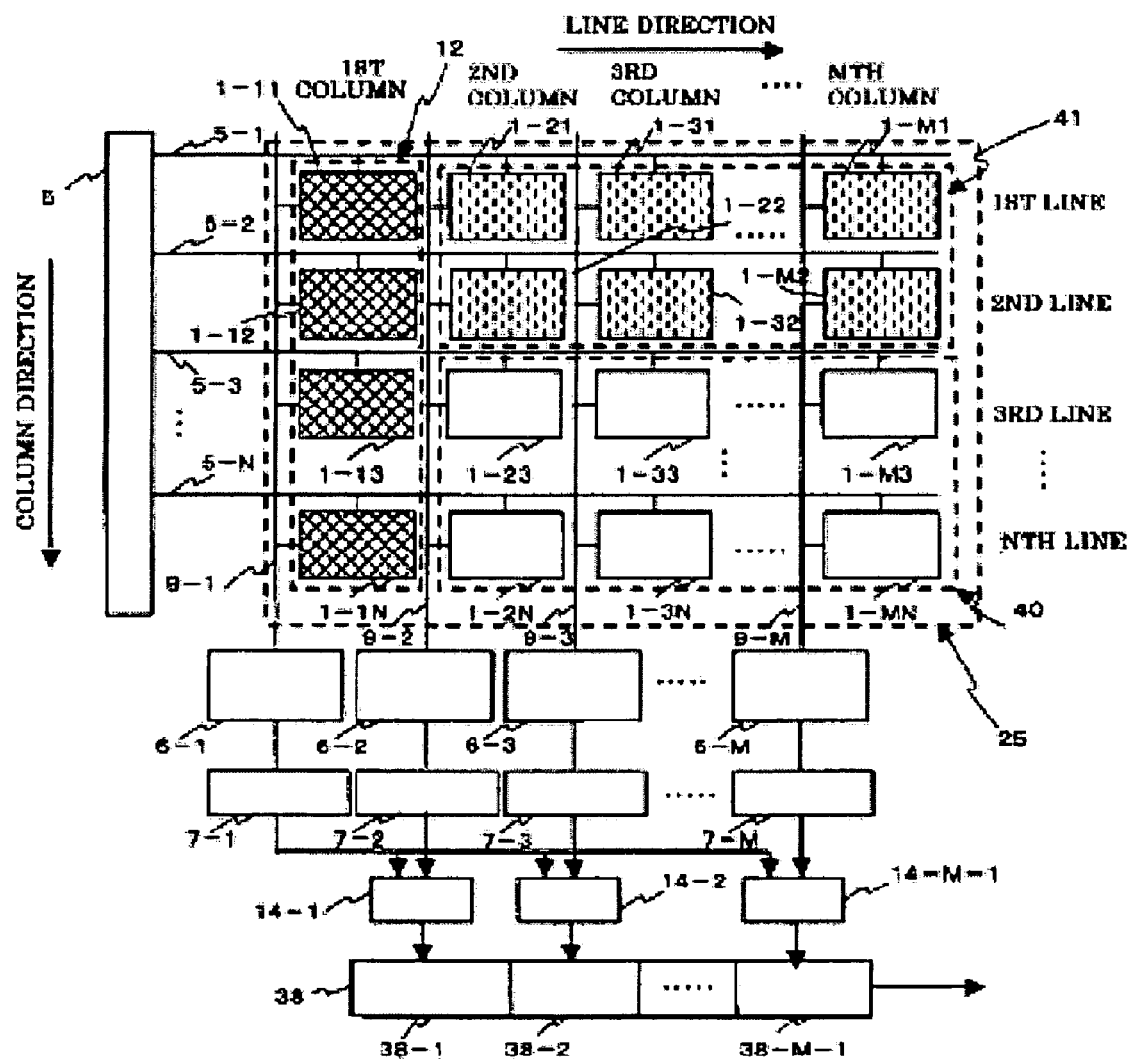
FIG. 8A is a block diagram of a flat panel detector in a modification of the first embodiment.

Next, a modification of the first embodiment will be explained. The modification applies the first embodiment to a flat panel detector which reduces a dark current noise as disclosed in Japanese Patent Publication (Kokai) No. 2001-34032, the entire contents of which are incorporated herein by reference. FIG. 8A shows a flat panel detector 25 and its circumference circuit. After the X-ray is irradiated, the gate driver 5 outputs the driving pulse to each detection element, the electric charge accumulated in the detection element is read out to the output wire 9-1 to 9M similar to the flat panel detector shown in FIG. 4 in the first embodiment. Furthermore, the electric charges read out to the output wire 9-1 to 9M are sent to the A/D converter 71 to 7M via the charge/voltage converter 61 to 6M. The flat panel detector 25 includes a mask for blocking the X-ray on a surface of the first column detection elements 1-11, 1-12, 113 . . . 11N. The electric charges on the first column covered by the mask are read out and inputted to first terminals of subtraction units 141 to 14M via the A/D converters 71. On the other hand, the electric charges accumulated in the detection elements on the second to Mth columns not covered by the mask are read out and inputted to second terminals of subtraction units 141 to 14(M-1) via the A/D converter 72 to 7M. The subtraction unit 141 to 14(M-1) respectively subtracts an output signal of the A/D converter 71 from outputs of A/D converter 72 to 7M. A result of the subtraction is temporally stored in memories 381 to 38(M-1) of the parallel/serial converters 38 and is stored in the image memory unit 16.

While the X-ray is not irradiated, the electric charge caused by the dark current (hereinafter called as a noise charge) accumulates in the storage capacitor 3. This noise charge that is different from the stray charge generated immediately after the TFT turns to the OFF state as the noise chargeconstantly accumulates while the TFT remains in the OFF state. In order to reduce influence of the noise charge, in the above described in Japanese Patent Publication (Kokai) No. 2001-34032, the mask for blocking the X-ray is provided on the surface of the detection element 1 on the valid area 40. The following explanation is one example, for explaining a principle of the dark current reduction, that the mask for blocking the X-ray is provided on the first column detection elements 1-11, 1-12, 113 . . . 11N, and the mask is not provided on the second column detection elements 1-21, 1-22, 123 . . . 12N.

Figure 8B:
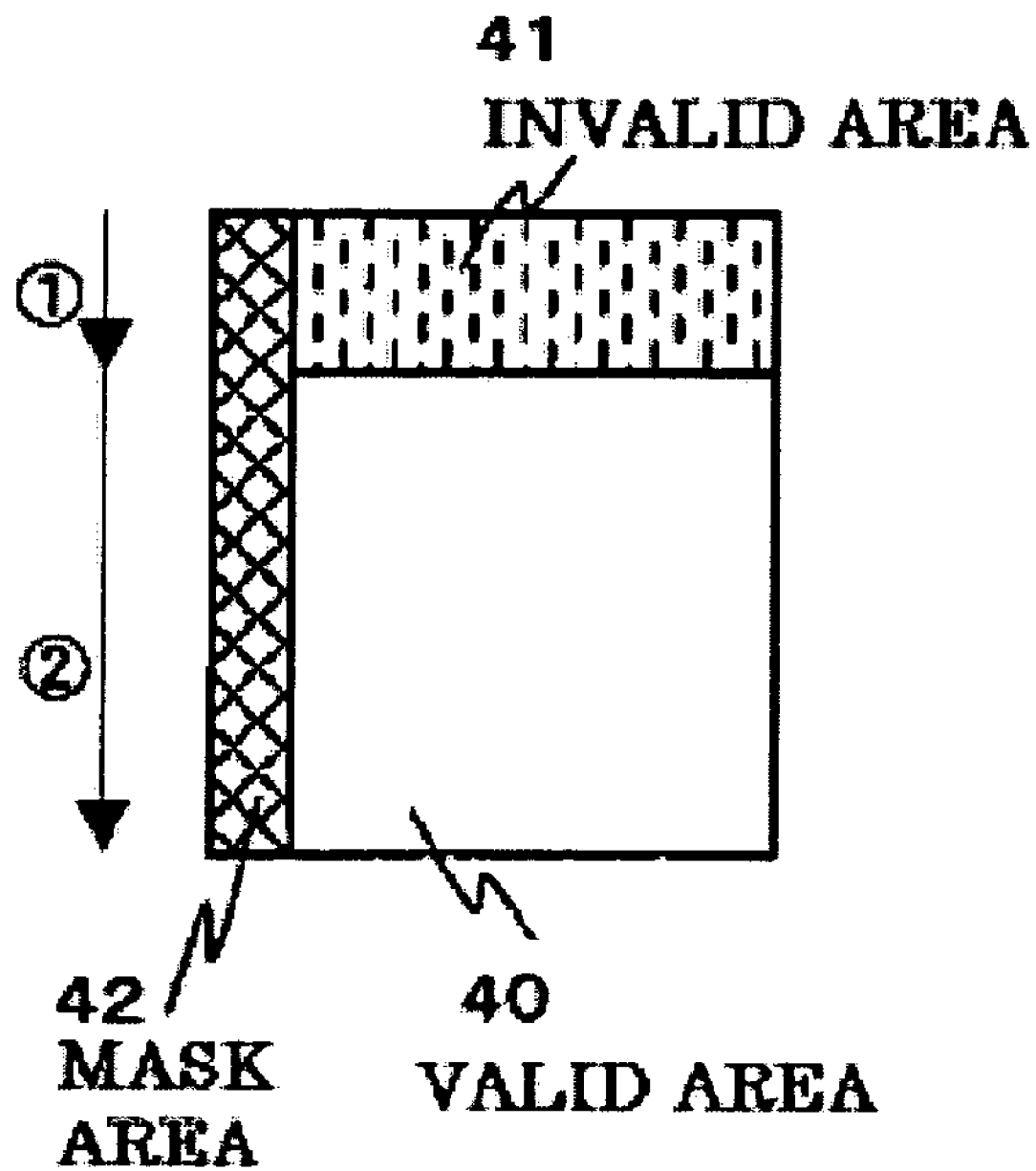
FIG. 8B shows a mask area on the flat panel detector in the modification.

When the X-ray penetrate the patient 13 and irradiates to the flat panel detector 25, the detection elements 1-21, 1-22, 123 . . . 12N accumulates the signal charge corresponding to the amount of the X-ray, while the detection elements 1-11, 1-12, 113 . . . 11N does not accumulate the signal charge because of the mask. Until the signal charges accumulated in the detection elements 1-21, 1-22, 123 . . . 12N are read out to the output wire 9-2 by the driving pulse of the gate driver 5 after the X-ray is irradiated, these detection elements accumulate noise charges caused by the dark current. Thus, the noise charges are added to the signal charges of the detection elements 1-21, 1-22, 123 . . . 12N. On the other hand, in the detection elements 1-11, 1-12, 113 . . . 11N, only the noise charges are accumulated, and the noise charges are read out to the output wire 9-1 by the driving pulse of the gate driver 5. The electric charges read out to the output wires 9-1 and 9-2 are converted to the voltage by the charge/voltage converter 61 and 62, and are A/D converted by the A/D converter 71 and 72 to be inputted to the subtraction units 141. By the subtraction units 141, the common noise charges are subtracted, and only the signal charges are stored in the image memory unit 16 via the memory 381 of the parallel/serial converter 38. Similarly, regarding the 3rd to Mth columns, by subtracting the voltage signal corresponding to the electric charge outputted to the output wire 9-1 from the voltage signal corresponding to the electric charge outputted to the output wire 93 to 9M to reduce the noise charge, only the signal charge is stored in the image memory unit 16 via the memory 381 of the parallel/serial converter 38. In this modification, as shown in FIG. 8B, the first column detection elements 1-11, 1-12, 113 . . . 1N are on a mask area 42 where the mask covers, the first line detection elements 1-11, 1-21, 131 . . . 1M1 and the second line detection elements 1-22, 132 . . . 1M2 are on the invalid are 41, and the remaining detection elements are on the valid 40. By using these three types of areas to drive the detection elements 1 similar to the first embodiment and by performing the subtraction, not only the noise charge can be reduced, but also the shading caused by the stray signal can be restrained. An explanation about the generation of the stray charge and the restraint of the shading is omitted, because it is similar to the first embodiment.

As described above, in the first embodiment and the modification, the detection elements on the invalid area 41 are read out in advance, and when the total stray charge is stabilized, the detection elements on the valid area 40 are read out to create the X-ray image. Thus, since the changing of the total stray charge added to the signal charge is low, the shading which appears on the X-ray image is restrained. In the first embodiment and the modification, the invalid area 41 is adjacent to the valid area 40, however the invalid area 41 may not be adjacent to the valid area 40. Furthermore, in FIG. 3, it is shown that the X-ray is irradiated to only to the valid area 40, but the X-ray may be irradiated to the invalid area 41. However, in a preferred embodiment, the X-ray is not irradiated to the invalid area or a mask is incorporated to reduce a X-ray dose for the patient.

Figure 9:
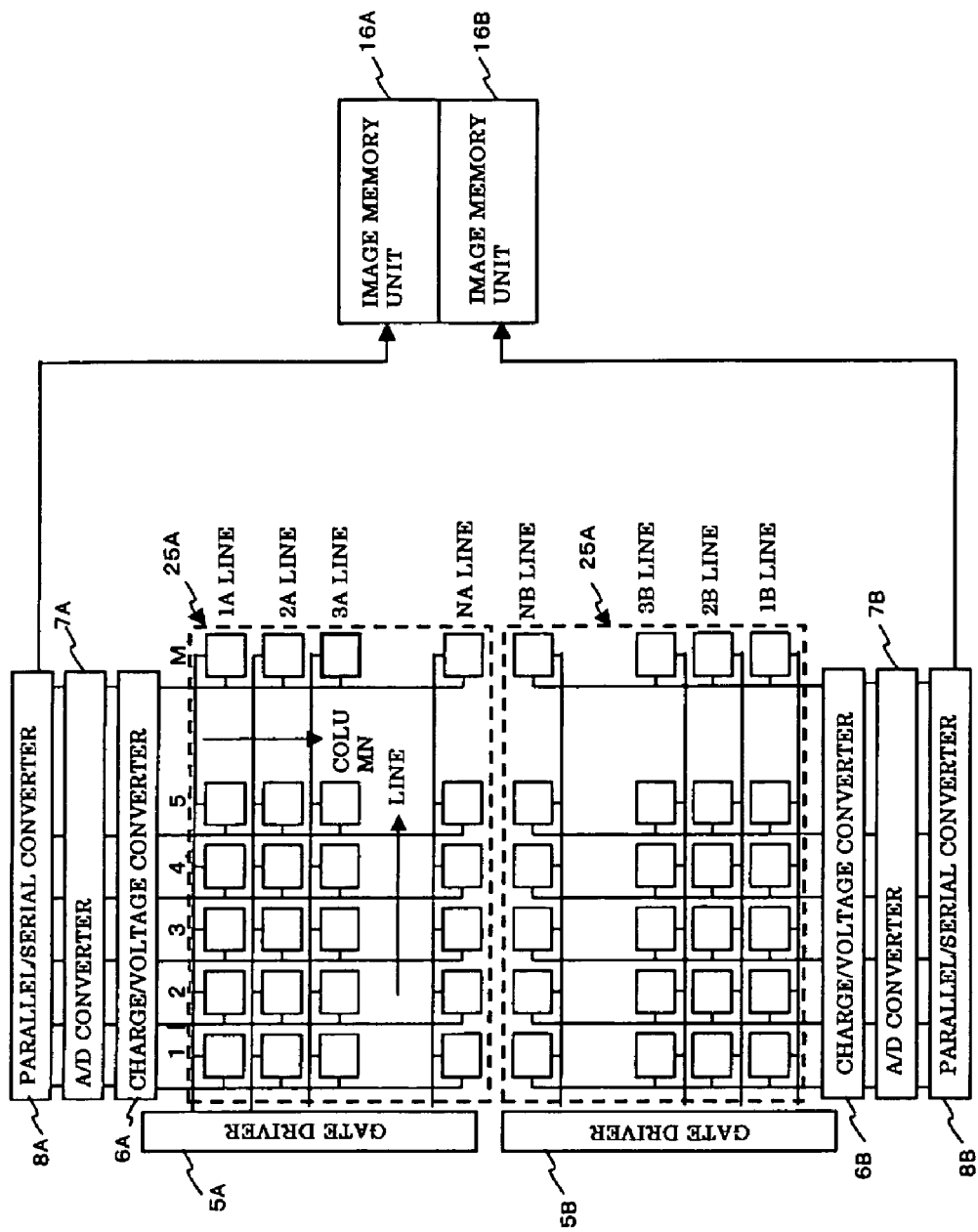
FIG. 9 is a block diagram of a flat panel detector in the second embodiment.

A second embodiment of the present invention will be explained, referring to FIG. 9. There is a real time function which displays the X-ray image in real time using the flat panel detector 25 as one of efficient functions. In order to improve the real time function, the flat panel detector 25 is separated to two detectors 25A and 25B, and the detection elements on each detector are read out in parallel. In the second embodiment, reduction of the shading using the above mentioned separating read out method is described. In the flat panel detector 25, the detector 25A includes M×NA detection elements, and the detector 25B includes M×NB detection elements. The detector 25A and 25B includes respective gate drivers 5A and 5B, respective charge/voltage converters 6A and 6B, respective A/D converters 7A and 7B, and respective parallel/serial converters 8A and 8B. The NA is may be N/2 and the NB may be N/2. The image memory unit 16 is similarly separated to an image memory unit 16A and an image memory unit 16B, the output signals of the parallel/serial converters 8A and 8B are respectively stored in the image memory unit 16A and 16B in parallel. In the detector 25A and 25B, driving terminals (namely the gate terminals of the TFT) of the M detection elements 1 are commonly connected to the output terminal of the gate driver 5. Output terminals (namely the drain terminals of the TFT) of the NA and NB detection elements arranged in the column direction are commonly connected to the input terminals of the respective charge/voltage converters 6A and 6B in the image data generation unit 26.

Figure 10:
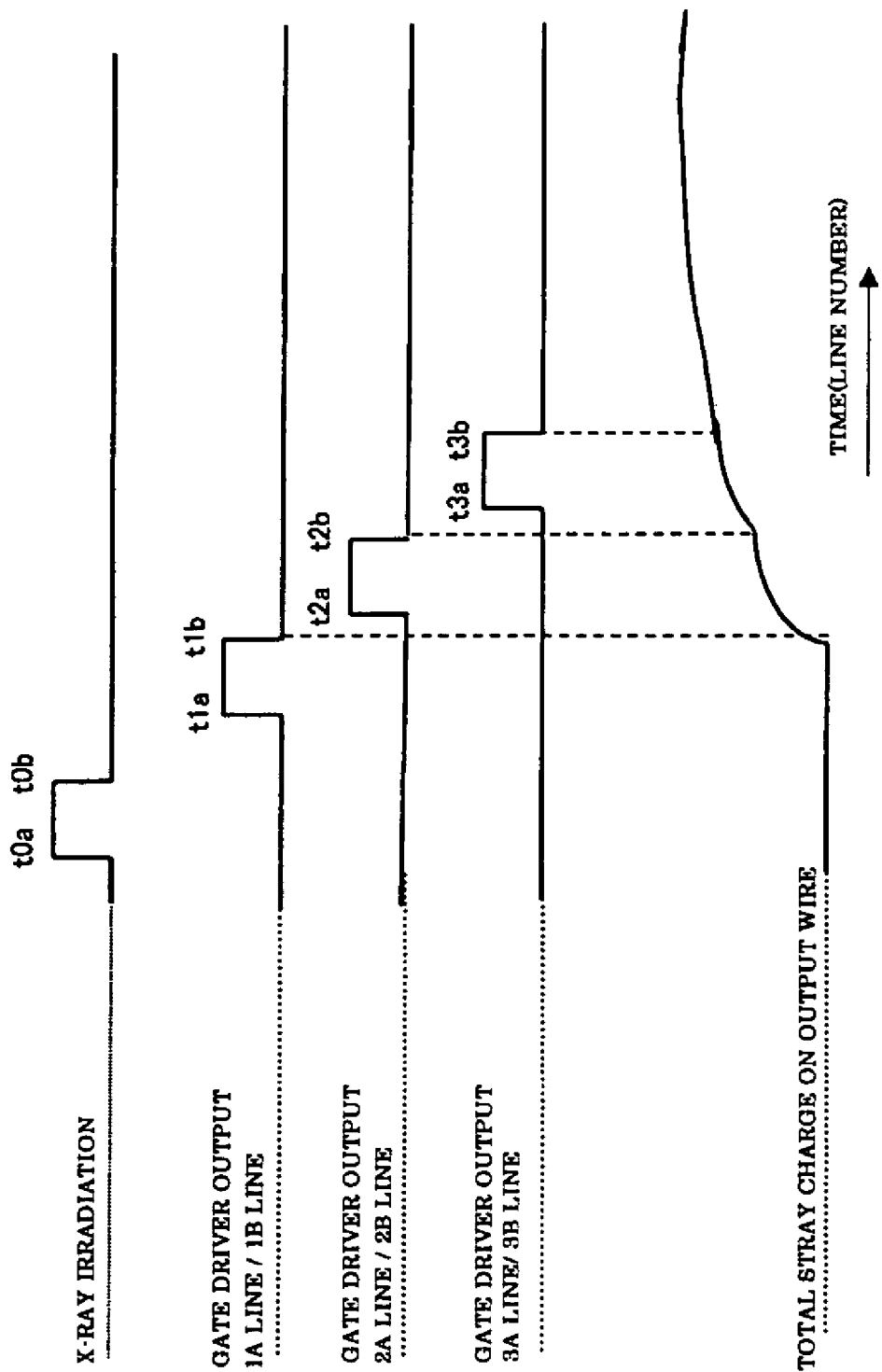
FIG. 10 is a timing chart for explaining an order of generation of a stray charge in the second embodiment.

FIG. 10 shows the driving signal of the gate driver 5 for one variant of the second embodiment. A first row of FIG. 10 shows a timing of the X-ray irradiation, a second row shows a timing of the output from the gate terminal for driving the detection elements on 1A and 1B lines. Similarly, the third row shows the timing of the output from the gate terminal for driving the detection elements on 2A and 2B lines and the forth row shows the timing of the output from the gate terminal for driving the detection elements on 3A and 3B lines. The total stray charge is shown on the fifth row of FIG. 10. Thus, in one embodiment the second embodiment, the detector 25A is arranged adjacent to the detector 25B, and the detection elements are read out on each detector from an opposite line against an adjacent line to the adjacent line in order. Based on the control signal from the system control unit 17, the X-ray generating unit 12 irradiates the X-ray to the patient 13 during t0a to t0b, and the flat panel detector 25A and 25B detect the X-ray penetrating through the patient 13 and accumulate the signal charges corresponding to the amount of the X-ray. When the X-ray irradiation is completed, the M detection elements on the line 1A and 1B are driven by the gate drivers 5A and 5B during t1a to t1b, and the accumulated signal charges are outputted to the charge/voltage converter 6A and 6B. The outputted signal charges are stored in the image memory unit 16A and 16B via the charge/voltage converter 6A and 6B, via the A/D converters 7A and 7B, and via respective parallel/serial converters 8A and 8B.

During t2a to t2b, the gate driver 5A and 5B drives the M detection elements on the line 2A and 2B, and the accumulated signal charges in these detection elements are outputted to the charge/voltage converter 6A and 6B. At this time, the stray charges from the line 1A and 2B are outputted and added to the signal charges of the line 2A and 2B. The added electric charges are stored in the image memory unit 16A and 16B via the charge/voltage converter 6A and 6B, via the A/D converters 7A and 7B, and via respective parallel/serial converters 8A and 8B. Similarly, the signal charges and the stray charges on the line 3A and 3B, 4A and 4B . . . NA and NB are stored in the image memory unit 16A and 16B via the charge/voltage converter 6A and 6B, via the A/D converters 7A and 7B, and via respective parallel/serial converters 8A and 8B. In the image memory unit 16A and 16B, the X-ray image is created, and the system control unit 17 controls the display image memory 36 of the display unit 21 to temporally store the X-ray image, and controls the monitor 33 to display the X-ray image changed to the TV format by the D/A converter 31 and the display circuit 32.

Figure 11:
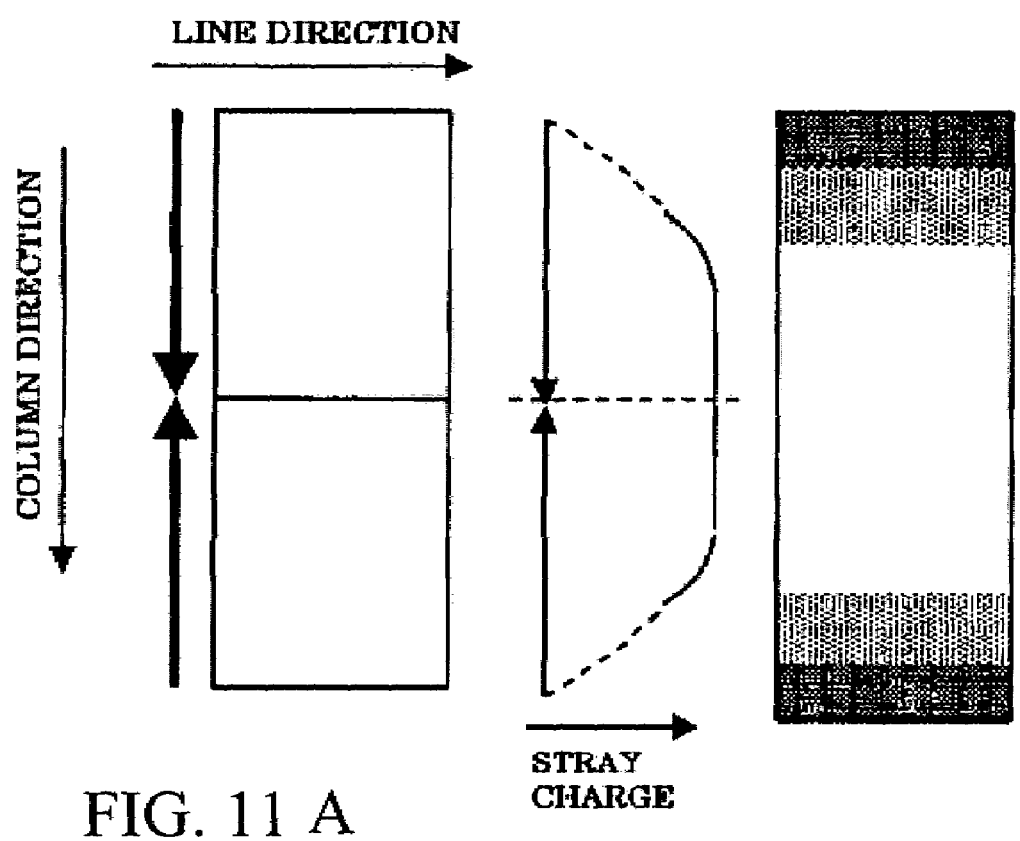
FIG. 11A shows a shading area on an X-ray image in the second embodiment.
FIG. 11B shows a shading area on an X-ray image in a prior art.
Figure 11B:
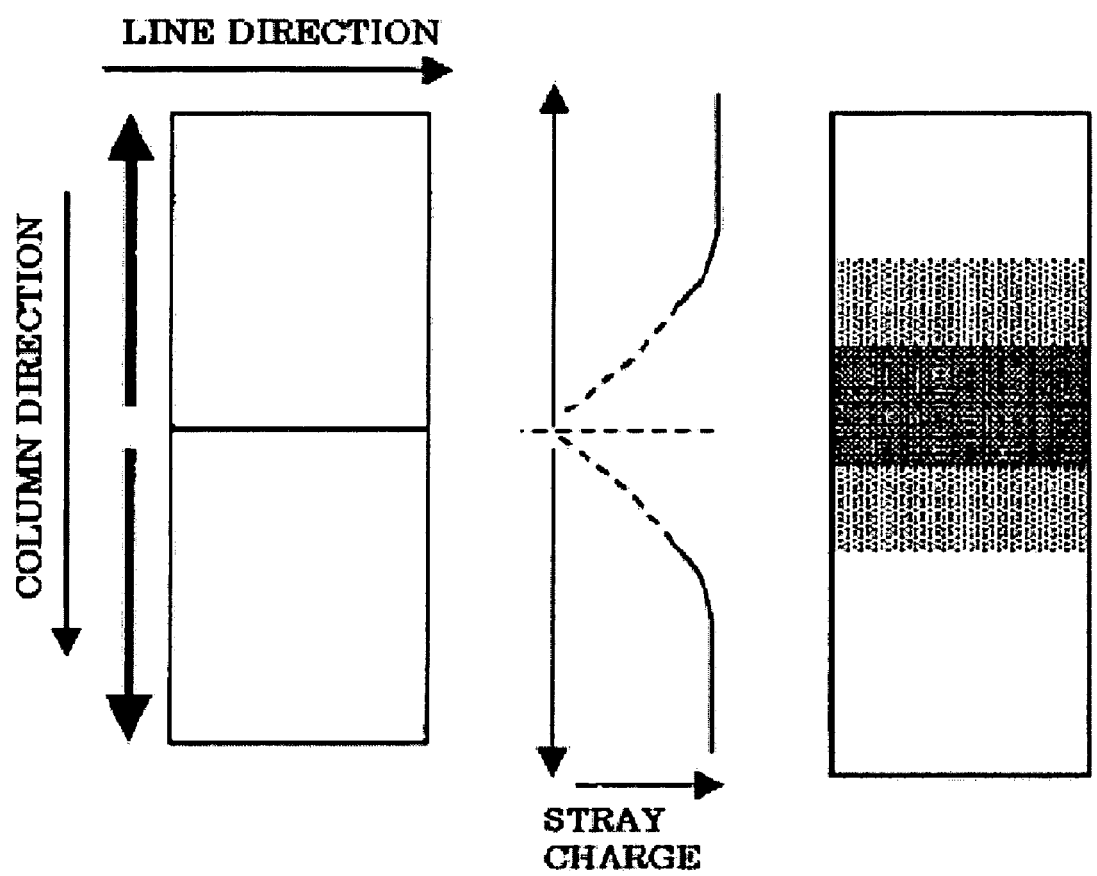

Next, an advantage is described when the detector 25A and 25B are read out from the opposite line to the adjacent line as compared to a read out from the adjacent line to the opposite line. FIG. 11A shows the shading characteristic of the second embodiment, and FIG. 11B shows the shading characteristic of a conventional method where the detectors are read out from the adjacent line to the opposite line. In FIG. 11A, a left side view shows the X-ray detector 25 and thick arrow lines indicate directions of the reading. A middle view of FIG. 11A shows the total stray charge characteristic, and a right side view indicates the X-ray image where the shading appears. When the detection elements are read out from the line 1A to NA in the flat panel detector 25A and the detection elements are read out from the line 1B to NB in the flat panel detector 25B, as shown in the left side view of FIG. 11A, the outputted total stray charges are comparable on a central area near the adjacent line, as shown in the middle view of FIG. 11A. On the other hand, when the detection elements are read out from the line NA to 1A in the flat panel detector 25A and the detection elements are read out from the line NB to 1B in the flat panel detector 25B, as shown in the left side view of FIG. 1B, the total stray charge on line NA and NB changes significantly and a large depression appears on the central area near the adjacent line, as shown in the middle view of FIG. 11B. That is, as shown in the right side views of FIG. 11A, when the read-out direction is from the opposite line to the adjacent line, the shading appears on both edge areas to the opposite line (an upper and lower edges in FIG. 11A). On the other hand, as shown in the right side views of FIG. 11B, when the read-out direction is from the adjacent line to the opposite line, the shading appears on the central area.

In general diagnostic imaging, the most important part for diagnosis is located on the central area. In the second embodiment, the appearance of the shading is limited to the edge area since the reading direction is from the opposite line to the adjacent line. Therefore, influence of the shading to the diagnosis can be reduced. In the above, although the detector is separated to two parts, a number of the separation may be not limited. That is, other embodiments exist where the detector is separated into more than two parts. Also, there are other embodiments where the sequence of reading the rows is varied in order to produce a predetermined effect.

Figure 12:
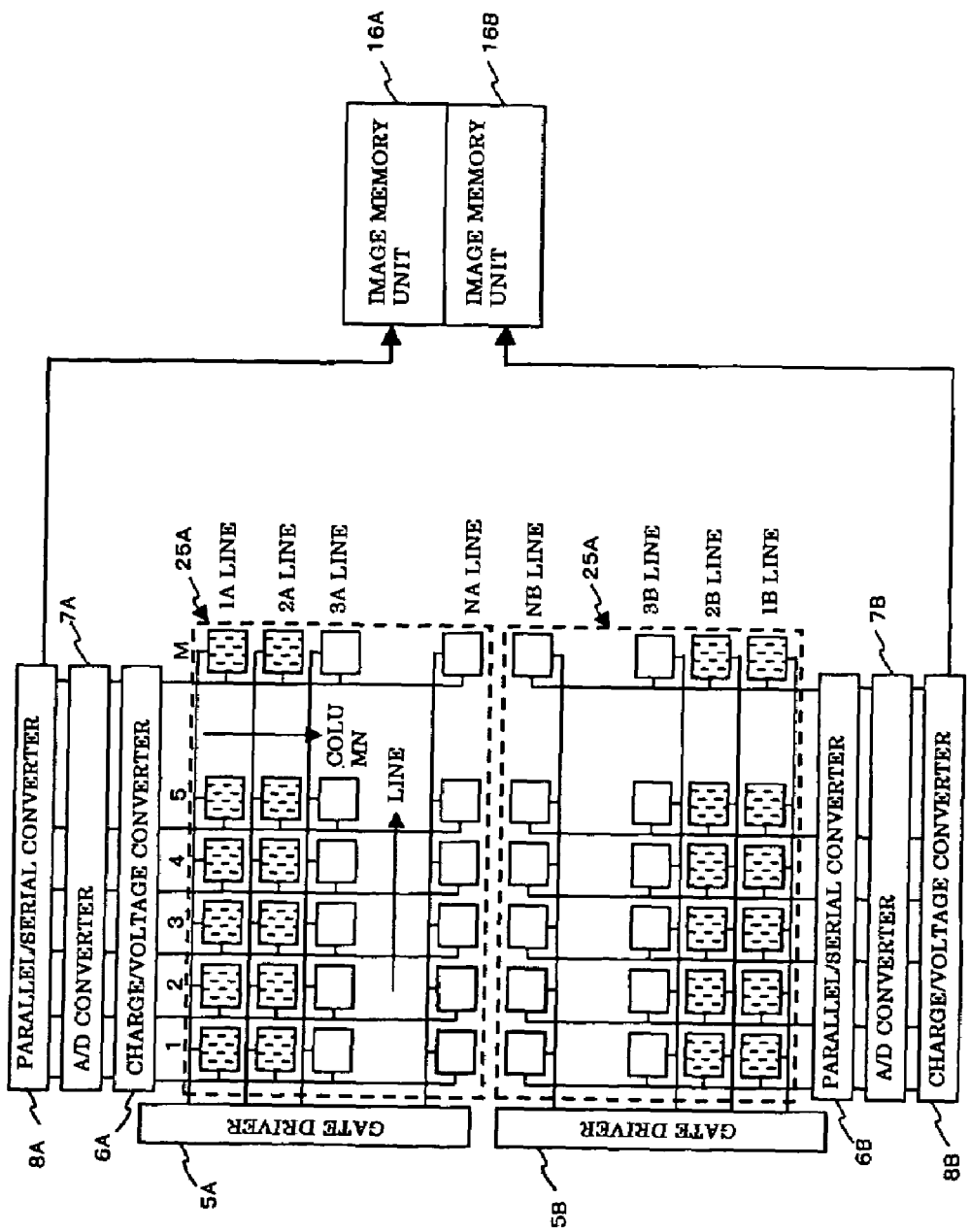
FIG. 12 is a block diagram of a flat panel detector in the third embodiment.

A third embodiment of the present invention will be explained, referring to FIG. 12. In the third embodiment, in order to reduce the influence of the shading, a combination of the invalid area 41 in the first embodiment and the separation of the detector in the second embodiment is described. In FIG. 12, the flat panel detector 25A including the M×NA detection elements and the flat panel detector 25B including the M×NB are adjacently positioned in the line direction. The flat panel detector 25A and 25B include respective gate driver 5A and 5B, respective charge/voltage converters 6A and 6B, respective A/D converters 7A and 7B, and respective parallel/serial converters 8A and 8B. The NA may be N/2 and the NB may be N/2. The image memory unit 16 is similarly separated to an image memory unit 16A and an image memory unit 16B, the output signals of the parallel/serial converters 8A and 8B are respectively stored in the image memory unit 16A and 16B in parallel. The system control unit 17 reads out the X-ray image data from the image memory unit 16A and 16B, controls the display image memory 36 of the display unit 21 to temporally store the X-ray image, and controls the monitor 33 to display the X-ray image changed to the TV format by the D/A converter 31 and the display circuit 32. In the flat panel detector 25A of the third embodiment, the first line 1A and second line 2A are on the invalid area 41, and the third line 3A to Nth line NA are on the valid area 40. The detection elements on the first line 1A and second line 2A are read out prior to the detection elements on the third line 3A to Nth line NA. Similarly, in the flat panel detector 25B, the first line 1B and second line 2B are on the invalid area 41, and the third line 3B to Nth line NB are on the valid area 40. The detection elements on the first line 1B and second line 2B are read out prior to the detection elements on the third line 3B to Nth line NB. Since a method for reading the electric charges from each detector 25A and 25B similar to the first embodiment, an explanation is omitted.

Figure 13:
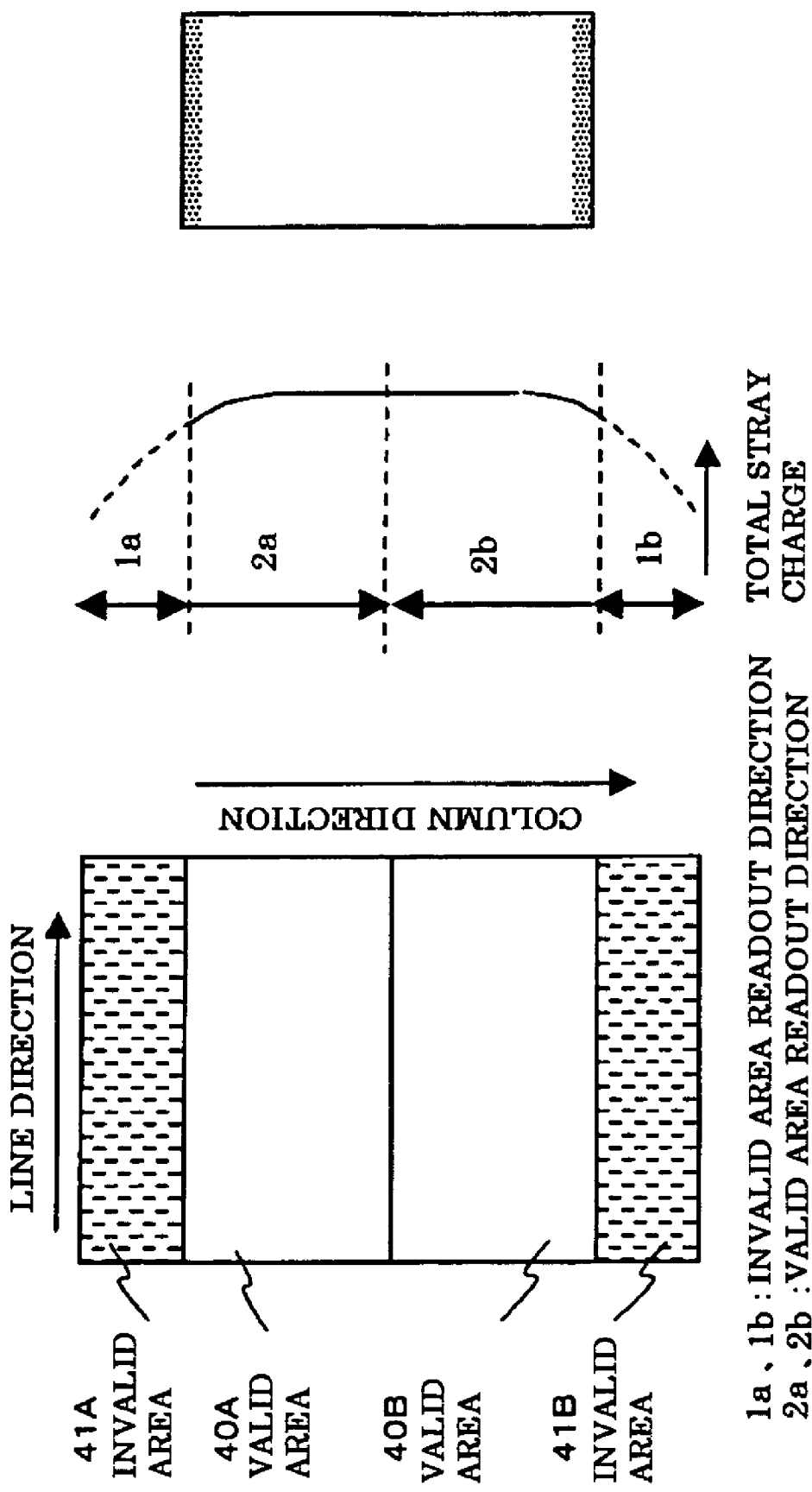
FIG. 13 shows a shading area on an X-ray image in the third embodiment.

FIG. 13 shows the shading characteristic in the third embodiment, and a left side view of FIG. 13 shows the flat panel detector 25A and 25B which include the invalid area 41A and 41B and the valid areas 40A and 40B. A middle view of FIG. 13 shows the total stray charge characteristic of the third embodiment, and a right side view indicates the X-ray image where the shading appears. The read-out direction of the electric charge from the valid areas 40A and 40B is the direction to the adjacent line as well as the second embodiment. The degree of the shading depends on a number of lines on the invalid area 41 but hardly depends on the read-out direction. Therefore, the read-out direction of the electric charge on the invalid areas 41A and 41B is vice versa.

Figure 14:
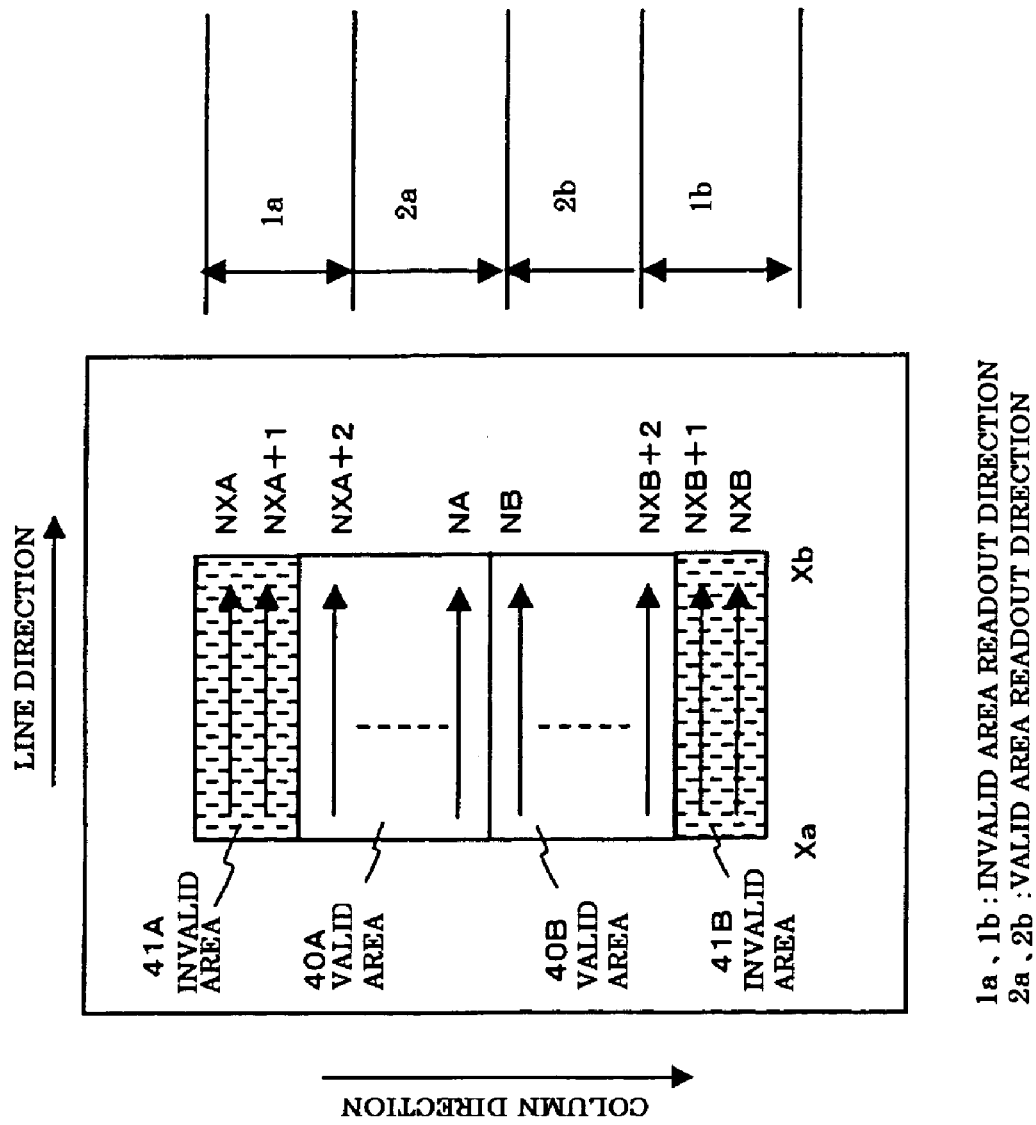
FIG. 14 shows a shading area on an X-ray image in a first modification of the third embodiment.

In FIG. 14, the read-out direction and area of a first modification of the third embodiment is shown. In the first modification, the operator sets the area of the X-ray irradiation smaller than the maximum imaging area, and the set area is positioned on a center area near the adjacent line. The flat panel detectors 25A and 25B similar to the flat panel detector shown in FIG. 12 and its circumference circuits may be used, and a driving method of the circumference circuits, such as the gate driver 5, is changed. In the flat panel detectors 25A and 25B, the central areas near the adjacent line are the valid areas 40A and 40B, and the edge areas are the invalid areas 41A and 41B. For example, the lines of NXA to NXA+1 and the lines of NXB to NXB+1 are set as the invalid area 41, and the lines of NXA+2 to NA and the lines of NXB+2 to NB are set as the valid area 40. The system control unit 17 sends the control signal to the gate drivers 5A and 5B, and the gate drivers 5-1A and 5-1B drive the lines of NXA to NXA+1 on the invalid are 41 prior to the lines of NXA+2 to NA and NXB+2 to NB on the valid area 40. Subsequently, the signal charge and the stray charge on the valid area 40 are outputted to the output wires 9-1 to 9M.

The signal charge and the stray charge which are obtained during driving the lines of NXA+2 to NA on the valid area 40 are stored in the image memory unit 16 via the charge/voltage converters 6, the A/D converters 7 and the parallel/serial converter 38. The system control unit 17 reads out the image data from the image memory unit 16, and controls the display image memory 36 of the display unit 21 to temporally store the X-ray image data. The monitor 33 displays the X-ray image changed to the TV format by the D/A converter 31 and the display circuit 32. As described above, in the third embodiment, by combining the invalid area 41 in the first embodiment and the separation of the detector in the second embodiment, the influence of the shading can be reduced. In the first modification of the third embodiment, the small imaging area can be imaged in short time and the shading is restrained. In the third embodiment, the read-out direction is from the opposite line to the adjacent line of the flat panel detector 25A and 25B, however the read-out direction may be changed in further variations of the third embodiment. That is, when a characteristic of the total stray charge is almost flat, the electric charge on the valid area 41A and 41B may be read out in each direction to reduce the shading on the X-ray image as shown as arrows 1*a* and 1*b* in FIG. 14. And also the read-out direction on the invalid area can be each direction.

Figure 15A:
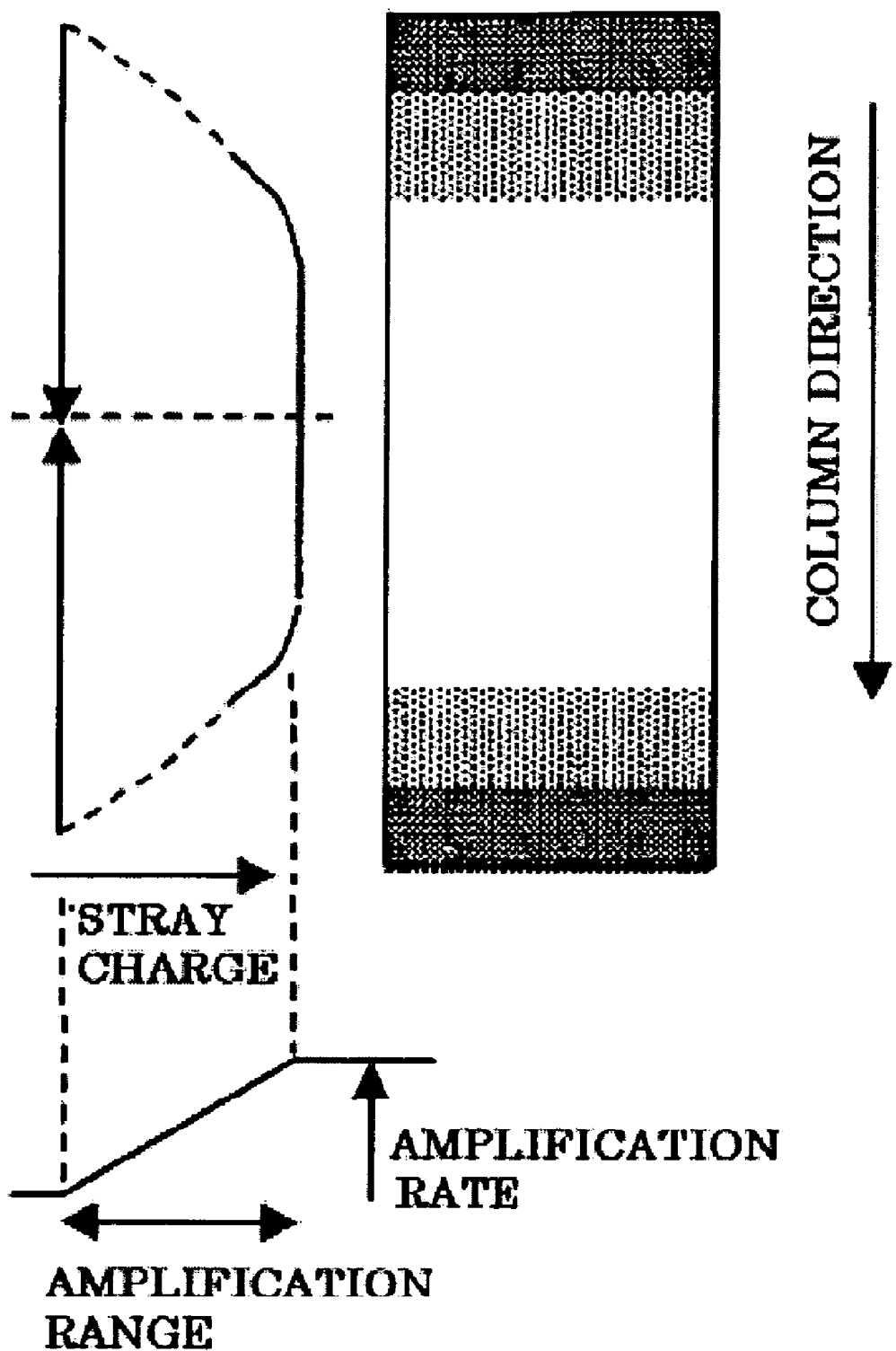
FIG. 15A shows a shading area on an X-ray image in the third embodiment.
Figure 15B:
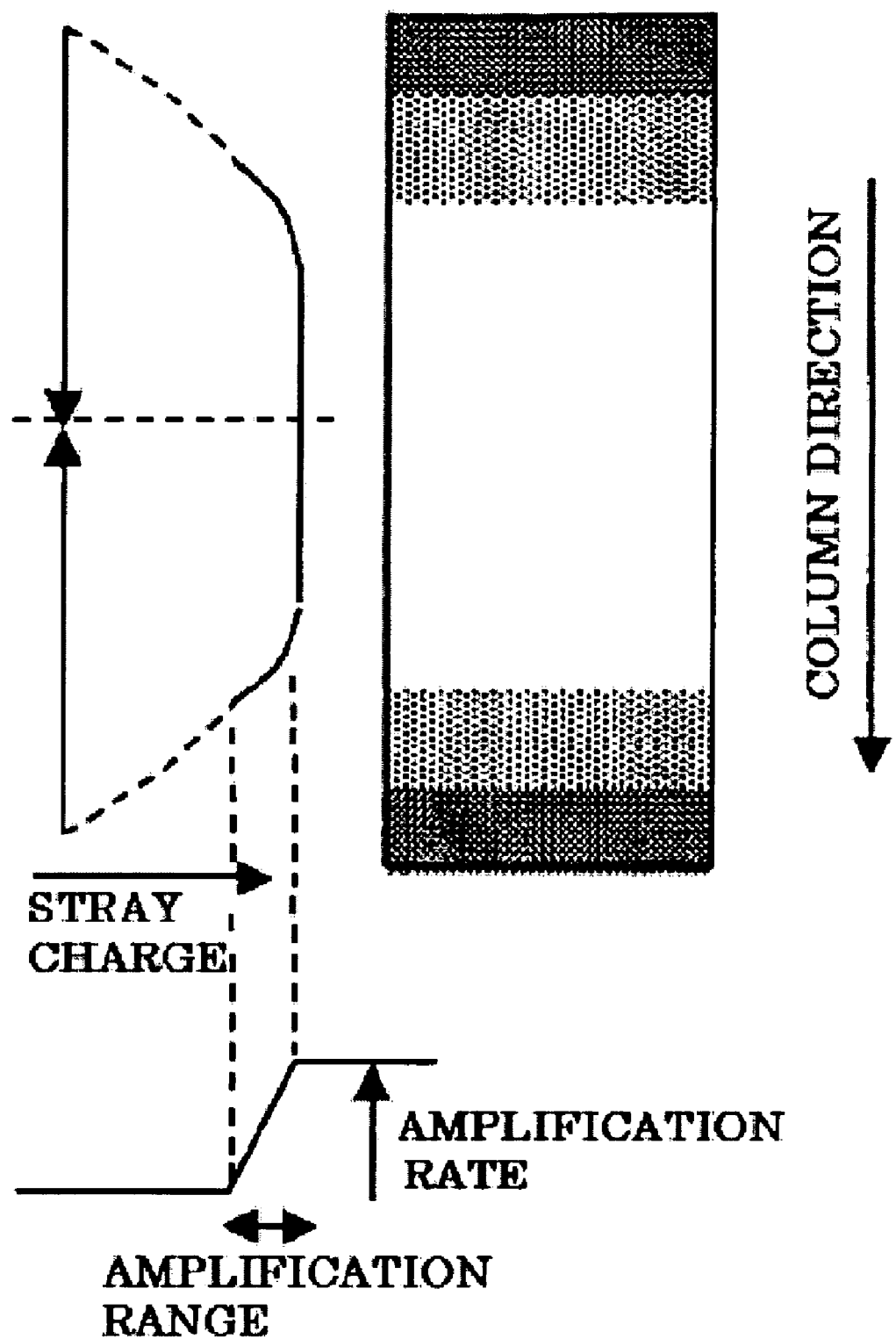
FIG. 15B shows a shading area on an X-ray image in a second modification of the third embodiment.

A second modification of the third embodiment will be explained referring FIGS. 15A and 15B. The second modification is related to an amplification range of the A/D converter 7. An explanation of features common with the third embodiment are omitted. In the second modification of the third embodiment, the amplification range of the A/D converter 7 is shown in FIG. 15A. An upper right side view indicates the X-ray image where the shading appears, and an upper left side view shows the total stray charge characteristic. In this time, the amplification range of the A/D converter 7 is shown in a lower left side view of FIG. 15A, and the amplification range covers almost all signals obtained on both of the invalid area 41 and the valid area 40 in the flat panel detector 25. On the other hand, in the second modification, the A/D converter 7 has the amplification range such that the signal obtained on the invalid area 41 is cut and the signal obtained on the valid are 40 is amplified as shown in FIG. 15B. Thus, the difference between signals obtained on the valid area 40 is emphasized, and a contrast of the X-ray image is improved.

Figure 15C:
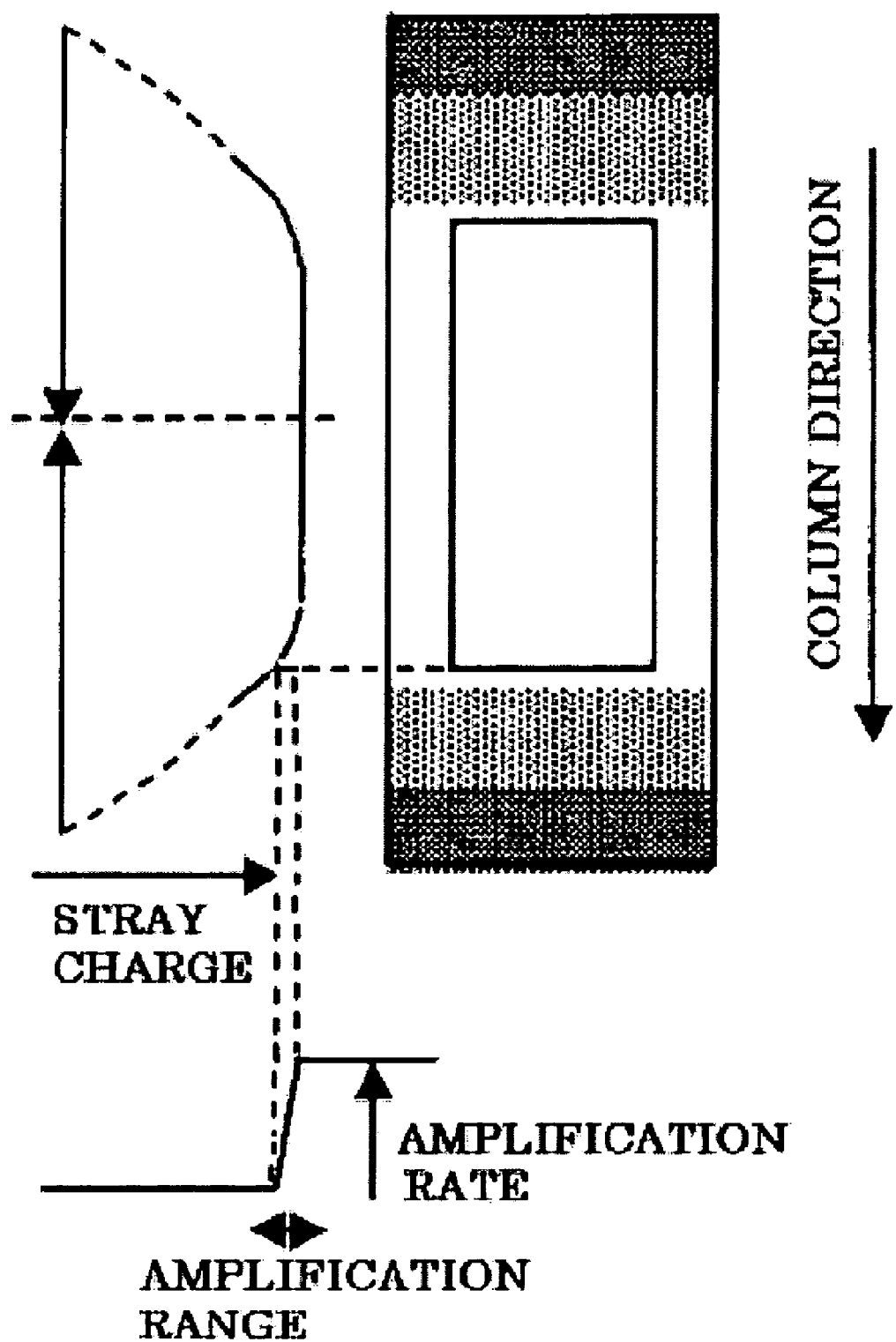
FIG. 15C shows a shading area on an X-ray image in a third modification of the third embodiment.

In a third modification of the third embodiment, the amplification range is changed based on the imaging area. As shown FIG. 15C, in the third modification, an imaging area smaller than the maximum area is set similar to the first modification. In detail, an appropriate amplification range of the A/D converter 7 is measured by the imaging area in advance, and is stored in the system control unit 17 as a table data. When the operator sets the imaging area, the amplification range corresponding to the set imaging area is read out and set. Thus, since the amplification range of the A/D converter 7 is set based on the imaging area that the operator sets, a contrast of the X-ray image is improved.

In another modification, when the imaging area on a part of the valid area 40 is set comparable to the third modification, the signal charge on the invalid area 41 may be first read out, and then the signal charge on the whole valid area 40 may be read out. The signal charge on the imaging area may be subsequently selected from the charge signal on the valid area 40, and the image is created from the signal charge on the imaging area.

The present invention is not limited to the above embodiments, and various modifications may be made without departing from the spirit or scope of the general inventive concept. For example, in the above embodiment, the invalid area 41 is described as having two lines, however the invalid area 41 may be actually include dozens of lines. Moreover, in FIG. 9, FIG. 12 and FIG. 14, the detection elements on the two flat panel detectors 40A and 40B may be read out in parallel, and the number flat panel detectors may be more than two. Further, the position of the invalid area 41 is not limited to the side of the third line, but may be on the side of the Nth line. Also the valid area 40 may not be adjacent to the invalid area 41. In a preferred embodiment, the X-ray is irradiated only to the valid area 40 on the flat panel detector 25, however in another embodiment the X-ray may also be irradiated on the invalid area 41. The stray charge is hardly influenced whether the X-ray is irradiated or not. Also, the embodiments described in the Figures are arranged in rectangular shape with the directions associated with the gate wire and output wires orthogonally offset. However, other embodiments exist that comprise other patterns (e.g., circles, triangles, pentagons, etc.) where gate wire connects radially displaced detectors while the output wire connects circumferentially displaced detectors, where the sequence of reading co-centric groups of detectors is controlled by one or more gate controllers. Other more complicated reading patterns are also possible.

What is claimed is:

1. An X-ray diagnosis apparatus, comprising:
an X-ray source;
a first X-ray detector positioned in relation to the X-ray source, said first X-ray detector including a first plurality of detection elements which are arranged in a first direction and a second direction;
a first readout unit connected to the first X-ray detector and configured to read out electric charges from a second area of the first X-ray detector before reading out electric charges from a first area of the first X-ray detector;
a first signal converter connected to the readout unit and configured to convert the electric charge read out from the first area of the first X-ray detector to X-ray image data;
a second X-ray detector positioned in relation to the X-ray source, said second X-ray detector including a first plurality of detection elements which are arranged in the first direction and the second direction;
a second readout unit connected to the second X-ray detector and configured to read out electric charges from a second area of the second X-ray detector before reading out electric charges from a first area of the second X-ray detector;
a second signal converter connected to the readout unit and configured to convert the electric charge read out from the first area of the second X-ray detector to X-ray image data; and
a display unit connected to the first and second signal converters and configured to display the X-ray image data,
wherein the first and second readout units are controlled to read out the electric charges from the first area of the respective first and second X-ray detectors in parallel and from outer row to inner row.

2. The X-ray diagnosis apparatus according to claim 1, wherein the X-ray detector comprises:
a gate wire connecting the readout unit to a first subset of the plurality of detection elements, the first subset aligned in a first direction; and an output wire connecting the signal converter to a second subset of the plurality of detection elements, said second subset aligned in a second direction.

3. The X-ray diagnosis apparatus according to claim 2, wherein a number of the X-ray detection elements aligned in the first direction on the first area is equal to a number of the X-ray detection elements aligned in the first direction on the second area.

4. The X-ray diagnosis apparatus according to claim 2, wherein the first area is adjacent to the second area.

5. The X-ray diagnosis apparatus according to claim 4, wherein the readout unit comprises:
a readout unit configured to read out electric charge from a subset of the first area.

6. An X-ray diagnosis apparatus, comprising:
an X-ray source;
a first X-ray detector positioned in relation to the X-ray source and including a first plurality of X-ray detection elements arranged in a first direction and a second direction, said plurality of X-ray detection elements configured to convert detected X-rays to electric charges;
a controller operably connected to the first X-ray detector and configured to establish a setable imaging area within a first area of the first X-ray detector;
a controller input unit operably connected to the controller;
a first readout unit connected to the first X-ray detector and configured to read out an electric charge from an X-ray detection element from a second area of the first X-ray detector which is outside of the first area before reading out an electric charge from a detection element from the setable imaging area;
a first signal converter connected to the readout unit and configured to convert the electric charge read out from the X-ray detection element from the setable imaging area to X-ray image data;
a display unit connected to the signal converter and configured to display the X-ray image data;
a second X-ray detector positioned in relation to the X-ray source and including a second plurality of X-ray detection elements arranged in the first direction and the second direction, said second plurality of X-ray detection elements configured to convert detected X-rays to electric charges;
a second readout unit connected to the second X-ray detector and configured to read out an electric charge from an X-ray detection element from a second area of the second X-ray detector which is outside of a first area of the X-ray detector before reading out an electric charge from a detection element from the setable imaging area in the second X-ray detector, said setable imaging area in the second X-ray detector established by the controller; and
a second signal converter connecting the second readout unit to the display unit,
wherein the first and second readout units are controlled to read out the electric charges from the respective first and second X-ray detectors according to a predetermined reading pattern, including reading from the respective first areas of the first and second X-ray detectors in parallel and from outer row to inner row.

7. The X-ray diagnosis apparatus according to claim 6, wherein the readout unit comprises:
a readout unit configured to read out an electric charge of an X-ray detection element in a portion of the first area that is other than the setable imaging area.

8. The X-ray diagnosis apparatus according to claim 6, further comprising:
an amplifier connecting the read out unit to the signal converter, said amplifier configured to cut the electric charge read out from the X-ray detection element from the second area and to amplify the electric charge read out from the X-ray detection element from the setable imaging area.

9. The X-ray diagnosis apparatus according to claim 6, further comprising:
an amplifier connecting the read out unit to the signal converter, said amplifier configured to amplify the electric charge read out from the X-ray detection element from the setable imaging area in an amplification range based on a size parameter of the imaging area.

10. The X-ray diagnosis apparatus according to claim 6, wherein the X-ray detector comprises:
a gate wire connecting a first subset of the plurality of X-ray detection elements to the readout unit, said first subset aligned in the first direction; and
an output wire connecting a second subset of the plurality of X-ray detection elements to the signal converter, said second subset aligned in a second direction.

11. The X-ray diagnosis apparatus according to claim 10, wherein a number of the X-ray detection elements in the first direction on the first area is equal to a number of the X-ray detection elements in the first direction on the second area.

12. The X-ray diagnosis apparatus according to claim 10, wherein the first area is adjacent to the second area.

13. The X-ray diagnosis apparatus according to claim 12, wherein the readout unit comprises:
a read out unit configured to read out an electric charge from a detection element from a subset of the first area.

14. An X-ray diagnosis apparatus, comprising:
an X-ray source;
a first X-ray detector positioned in relation to the X-ray source and including a first plurality of detection elements arranged in a first direction and a second direction and configured to change a detected X-ray to an electric charge;
a first readout unit connected to the first X-ray detector and configured to read out an electric charge from a detection element on a second area of the first X-ray detector before reading out an electric charge from a detection element on a first area of the X-ray detector;
an amplifier connected to the X-ray detector and configured to cut the electric charge read out from the detection element on the second area and to amplify the electric charge read out from the detection element on at least a part of the first area;
a signal converter connected to the amplifier and configured to convert the amplified electric charge to an X-ray image data;
a display unit connected to the signal converter and configured to display the X-ray image data;
a second X-ray detector positioned in relation to the X-ray source and including a second plurality of X-ray detection elements arranged in the first direction and the second direction, said second plurality of X-ray detection elements configured to convert detected X-rays to electric charges;
a second readout unit connected to the second X-ray detector and configured to read out an electric charge from an X-ray detection element from a second area of the second X-ray detector which is outside of a first area of the X-ray detector before reading out an electric charge from a detection element from the setable imaging area in the second X-ray detector, said setable imaging area in the second X-ray detector established by the controller; and a second signal converter connecting the second readout unit to the display unit, wherein the first and second readout units are controlled to read out the electric charges from the respective first and second X-ray detectors according to a predetermined reading pattern, including reading from the respective first areas of the first and second X-ray detectors in parallel and from outer row to inner row.

15. An X-ray diagnosis apparatus, comprising:

an X-ray source;

a first X-ray detector positioned in relation to the X-ray source including a first plurality of detection elements arranged in a first direction and a second direction and configured to change a detected X-ray to an electric charge;

an input unit operably connected to the X-ray detector and configured to input an imaging area in the X-ray detector and corresponding to an object to be irradiated;

a first readout unit connected to the first X-ray detector and configured to read out the electric charge from a detection element on a second area of the first X-ray detector before reading out an electric charge from a detection element on a first area of the X-ray detector;

an amplifier connected to the X-ray detector and configured to amplify the electric charge read out from a detection element on the imaging area in an amplification range determined based on the imaging area;

a first signal converter connected to the amplifier and configured to convert the amplified electric charge to an X-ray image data;

a display unit connected to the signal converter and configured to display the X-ray image data;

a second X-ray detector positioned in relation to the X-ray source and including a second plurality of X-ray detection elements arranged in the first direction and the second direction, said second plurality of X-ray detection elements configured convert detected X-rays to electric charges;

a second readout unit connected to the second X-ray detector and configured to read out an electric charge from an X-ray detection element from a second area of the second X-ray detector which is outside of a first area of the X-ray detector before reading out an electric charge from a detection element from the setable imaging area in the second X-ray detector, said setable imaging area in the second X-ray detector established by the controller; and a second signal converter connecting the second readout unit to the display unit, wherein the first and second readout units are controlled to read out the electric charges from the respective first and second X-ray detectors according to a predetermined reading pattern, including reading from the respective first areas of the first and second X-ray detectors in parallel and from outer row to inner row.

16. A method for controlling an X-ray diagnosis apparatus, comprising:

irradiating an object with an X-ray;

detecting an X-ray penetrating through the object first changing the detected X-ray to an electric charge with a first X-ray detector including a first plurality of detection elements arranged in a first direction and a second direction;

first reading out an electric charge from a detection element on a second area of the first X-ray detector before reading out an electric charge from a detection element on a first area of the first X-ray detector;

first converting the electric charge read out from the first detection element of the first X-ray detector on the first area to X-ray image data;

second changing the detected X-ray to an electric charge with a second X-ray detector including a second plurality of detection elements arranged in the first direction and the second direction;

second reading out an electric charge from a detection element on a second area of the second X-ray detector before reading out an electric charge from a detection element on a first area of the second X-ray detector;

second converting the electric charge read out from the second detection element of the second X-ray detector on the first area to X-ray image data; and displaying the X-ray image data, wherein the first and second reading out are controlled to read out the electric charges from the respective first and second X-ray detectors according to a predetermined reading pattern including reading the first areas of the respective first and second X-ray detectors in parallel and from outer row to inner row.

* * * * *